United States Patent
Adachi et al.

(10) Patent No.: US 9,429,513 B2
(45) Date of Patent: Aug. 30, 2016

(54) SENSOR APPARATUS AND IMAGE FORMING APPARATUS INCORPORATING SAME

(71) Applicant: RICOH COMPANY, LTD., TOKYO (JP)

(72) Inventors: Kazuhiko Adachi, Miyagi (JP); Yoshihiro Oba, Miyagi (JP); Toshihiro Ishii, Miyagi (JP); Fumikazu Hoshi, Miyagi (JP); Sunao Chubachi, Miyagi (JP); Yoshihiro Misaka, Miyagi (JP)

(73) Assignee: RICOH COMPANY, LTD., Tokyo (JP)

( * ) Notice: Subject to any disclaimer, the term of this patent is extended or adjusted under 35 U.S.C. 154(b) by 4 days.

(21) Appl. No.: 14/454,052

(22) Filed: Aug. 7, 2014

(65) Prior Publication Data

US 2015/0062582 A1 Mar. 5, 2015

(30) Foreign Application Priority Data

Aug. 29, 2013 (JP) ................................. 2013-177459
Oct. 24, 2013 (JP) ................................. 2013-220721
May 15, 2014 (JP) ................................. 2014-101007

(51) Int. Cl.
*G01J 4/00* (2006.01)
*G03G 15/00* (2006.01)
(Continued)

(52) U.S. Cl.
CPC ............... *G01N 21/21* (2013.01); *G01B 11/06* (2013.01); *G01G 9/00* (2013.01); *G01N 21/4738* (2013.01);
(Continued)

(58) Field of Classification Search
CPC .. G01N 21/21; G01N 21/4738; G01N 21/59; G01B 11/06

USPC ................................................... 356/369, 630
See application file for complete search history.

(56) References Cited

U.S. PATENT DOCUMENTS 5,170,049 A * 12/1992 De Jonge ............ G01N 21/211
250/225
6,388,452 B1 * 5/2002 Picciotto ............. B41J 11/0035
324/452
(Continued)

FOREIGN PATENT DOCUMENTS

EP 1148315 A2 10/2001
EP 2458444 A2 5/2012
(Continued)

OTHER PUBLICATIONS

European Search Report dated Nov. 4, 2014 in corresponding European patent application No. 14 17 9380.2.
(Continued)

*Primary Examiner* — Kara E Geisel
*Assistant Examiner* — Dominic J Bologna
(74) *Attorney, Agent, or Firm* — Cooper & Dunham LLP

(57) ABSTRACT

A sensor apparatus includes an irradiation system with a light source configured to emit linearly polarized light of a first polarization direction onto a sheet-like object, in a direction oblique to a direction orthogonal to a surface of the object, a first photodetector arranged on an optical path of light that is emitted from the irradiation system and then is reflected at the object by regular reflection, a first optical element, arranged on an optical path of light reflected by diffuse reflection from an incidence plane of the object, configured to transmit linearly polarized light of a second polarization direction that is orthogonal to the first polarization direction, a second photodetector configured to receive light that has passed through the first optical element, and a detection unit configured to detect at least one of basis weight and thickness of the object.

18 Claims, 47 Drawing Sheets

(51) Int. Cl.
*G01N 21/21* (2006.01)
*G01B 11/06* (2006.01)
*G01G 9/00* (2006.01)
*G01N 21/47* (2006.01)
*G01N 21/59* (2006.01)

(52) U.S. Cl.
CPC .......... *G01N 21/59* (2013.01); *G03G 15/5029* (2013.01); *G01N 2201/062* (2013.01); *G01N 2201/0691* (2013.01); *G01N 2201/06113* (2013.01); *G01N 2201/105* (2013.01); *G03G 2215/00616* (2013.01); *G03G 2215/00738* (2013.01); *G03G 2215/00742* (2013.01)

(56) References Cited

U.S. PATENT DOCUMENTS

| | | | |
|---|---|---|---|
| 8,971,749 B2* | 3/2015 | Oba | G03G 15/5029 356/369 |
| 9,170,190 B2* | 10/2015 | Goto | G01N 21/21 |
| 2002/0030823 A1* | 3/2002 | Kobayashi | G01B 11/06 356/485 |
| 2009/0074435 A1 | 3/2009 | Murakami | |
| 2011/0032510 A1* | 2/2011 | Furnas | G01B 11/06 356/33 |
| 2011/0032523 A1* | 2/2011 | Furnas | G01B 11/06 356/364 |
| 2011/0222927 A1* | 9/2011 | Yamashina | G03G 15/2078 399/328 |
| 2011/0303848 A1* | 12/2011 | Jones | G01N 21/3563 250/340 |
| 2012/0134693 A1* | 5/2012 | Hoshi | G03G 15/5029 399/45 |
| 2013/0057861 A1 | 3/2013 | Ishii et al. | |
| 2013/0194573 A1 | 8/2013 | Ohba et al. | |
| 2013/0216245 A1 | 8/2013 | Hoshi et al. | |
| 2013/0216246 A1 | 8/2013 | Hoshi et al. | |
| 2013/0216247 A1 | 8/2013 | Oba et al. | |
| 2013/0228674 A1 | 9/2013 | Oba et al. | |

FOREIGN PATENT DOCUMENTS

| | | |
|---|---|---|
| JP | 10-160687 | 6/1998 |
| JP | 11-249353 | 9/1999 |
| JP | 2002-340518 | 11/2002 |
| JP | 2003-292170 | 10/2003 |
| JP | 2005-156380 | 6/2005 |
| JP | 2006-062842 | 3/2006 |
| JP | 2008-249714 | 10/2008 |
| JP | 2012-127937 | 7/2012 |
| JP | 2012-191582 | 10/2012 |

OTHER PUBLICATIONS

U.S. Appl. No. 14/199,056, filed Mar. 6, 2014.
U.S. Appl. No. 14/180,684, filed Feb. 14, 2014.

* cited by examiner

| BRAND | S1 | S2 | ST |
|---|---|---|---|
| A | ... — ... | ... — ... | ... — ... |
| B | ... — ... | ... — ... | ... — ... |
| C | ... — ... | ... — ... | ... — ... |
| D | ... — ... | ... — ... | ... — ... |

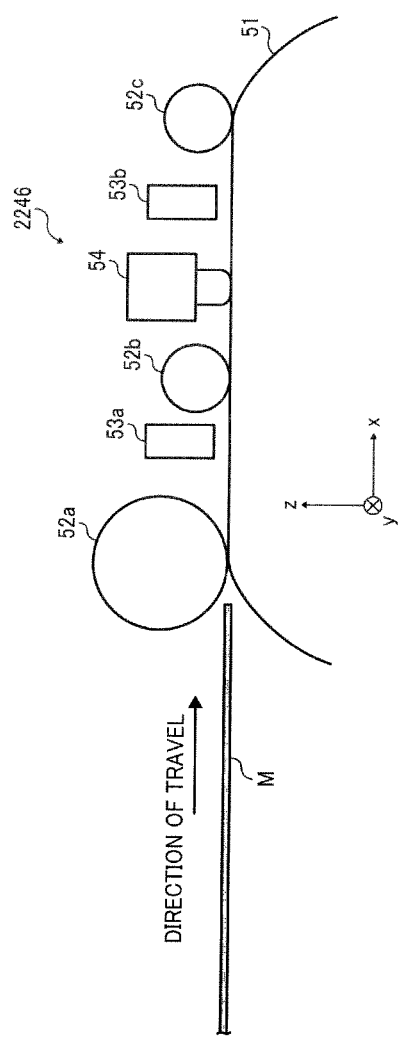

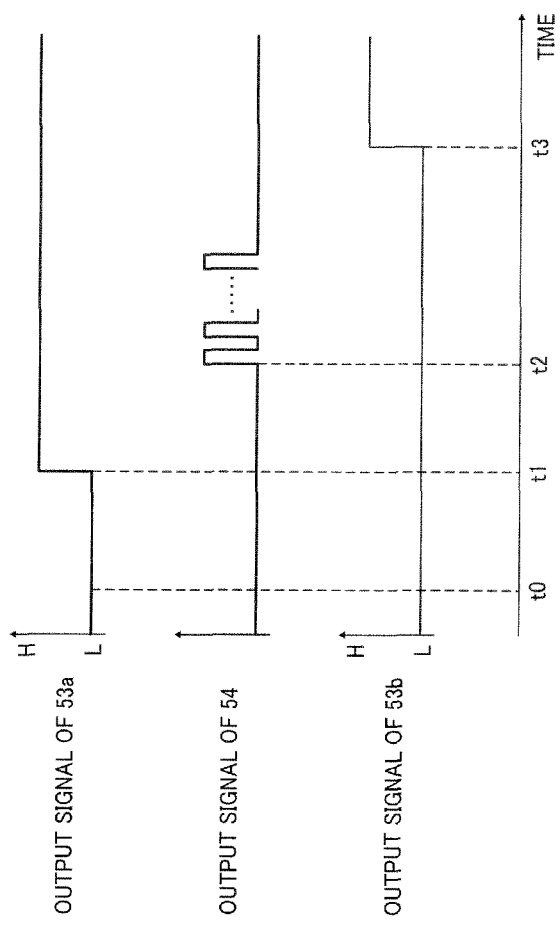

SENSOR APPARATUS AND IMAGE FORMING APPARATUS INCORPORATING SAME

CROSS-REFERENCE TO RELATED APPLICATIONS

This patent application is based on and claims priority pursuant to 35 U.S.C. §119(a) to Japanese Patent Application Nos. 2013-177459, 2013-220721, 2014-101007, filed on Aug. 29, 2013, Oct. 24, 2013, May 15, 2014, respectively, in the Japan Patent Office, the entire disclosure of which is hereby incorporated by reference herein.

BACKGROUND

1. Technical Field

Example embodiments of the present invention generally relate to a sensor apparatus and an image forming apparatus incorporating the sensor apparatus.

2. Background Art

Image forming apparatuses such as digital copying machines and laser printers form an image by transferring a toner image onto a recording medium, typified by printing paper, and heating and pressing (i.e., fixing) the image onto recording medium under certain specified conditions for fixation. When an image is formed, conditions for image formation such as development, transfer, and fixing conditions should be taken into consideration. In particular, when a high-quality image is to be formed, the conditions for image formation need to be set differently for each type of recording medium, because the quality of the image is heavily dependent on the recording medium material, thickness, moisture content, smoothness, and coating status. For example, irregularities in color may develop if fixing conditions are not proper for the type of recording medium.

Further, due to the development of image forming apparatuses and the diversification of expression in recent years, hundreds or more types of printing paper have become available as recording media, and a number of brands exist for each of these types for different basis weights and thickness. In order to achieve high-quality image formation, detailed conditions for image formation should be set for every one of these brands.

In recent years, the number of brands of paper is increasing for plain paper, coated paper typified by gloss coated paper, matte coated paper, and art paper, plastic sheet, and special paper whose surface is embossed.

SUMMARY

Embodiments of the present invention described herein provide an improved sensor apparatus including an irradiation system provided with a light source and configured to emit linearly polarized light of a first polarization direction onto a sheet-like object, in a direction oblique to a direction orthogonal to a surface of the object, a first photodetector arranged on an optical path of light that is emitted from the irradiation system and then is reflected at the object by regular reflection, a first optical element, arranged on an optical path of light reflected by diffuse reflection from an incidence plane of the object, configured to transmit linearly polarized light of a second polarization direction that is orthogonal to the first polarization direction, a second photodetector configured to receive light passed through the first optical element, and a detection unit configured to detect at least one of basis weight and thickness of the object.

Embodiments of the present invention described herein further provide an image forming apparatus incorporating the sensor apparatus.

BRIEF DESCRIPTION OF THE DRAWINGS

A more complete appreciation of exemplary embodiments and the many attendant advantages thereof will be readily obtained as the same becomes better understood by reference to the following detailed description when considered in connection with the accompanying drawings.

FIG. 42 illustrates the configuration of a thickness sensor according to the second example embodiment of the present invention.

FIG. 45 is a timing chart indicating the signals output from a thickness sensor, according to the second example embodiment of the present invention.

Figure 1:
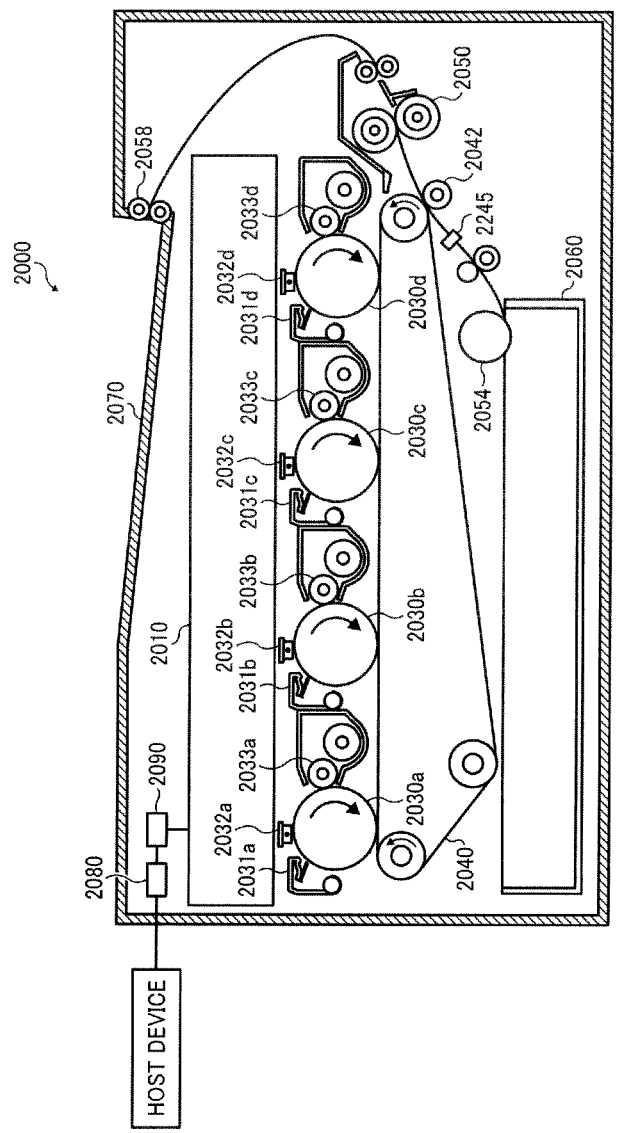
FIG. 1 is a schematic diagram the configuration of a color printer according to the first example embodiment of the present invention.

The accompanying drawings are intended to depict exemplary embodiments of the present disclosure and should not be interpreted to limit the scope thereof. The accompanying drawings are not to be considered as drawn to scale unless explicitly noted.

DETAILED DESCRIPTION

The terminology used herein is for the purpose of describing particular embodiments only and is not intended to be limiting of the present invention. As used herein, the singular forms "a", "an" and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

In describing example embodiments shown in the drawings, specific terminology is employed for the sake of clarity. However, the present disclosure is not intended to be limited to the specific terminology so selected and it is to be understood that each specific element includes all technical equivalents that have the same structure, operate in a similar manner, and achieve a similar result.

First Embodiment

The first example embodiment of the present invention is described with reference to FIGS. 1 to 18.

FIG. 1 is a schematic diagram illustrating the configuration of a color printer 2000 according to the first example embodiment of the present invention. The color printer 2000 is a tandem color printer that forms a full color image on a recording medium by superimposing multiple images of four colors (black, cyan, magenta, and yellow) on top of one another. Moreover, the color printer 2000 includes an optical scanner 2010, four photoreceptor drums 2030*a*, 2030*b*, 2030*c*, and 2030*d*, four cleaning units 2031*a*, 2031*b*, 2031*c*, and 2031*d*, four charging devices 2032*a*, 2032*b*, 2032*c*, and 2032*d*, four development rollers 2033*a*, 2033*b*, 2033*c*, and 2033*d*, a transfer belt 2040, a transfer roller 2042, a fixing device 2050, a paper feed roller 2054, an ejection roller 2058, a paper feed tray 2060, a paper output tray 2070, a communication controller 2080, an optical sensor 2245, and a printer controller 2090.

The communication controller 2080 controls bidirectional communication with a host device (for example, a personal computer (PC)) through a network or the like.

The printer controller 2090 includes, for example, a central processing unit (CPU), a read-only memory (ROM) in which a program described by CPU-readable codes and various kinds of data used for executing the program are stored, a random access memory (RAM) that serves as a working memory, an amplifier circuit, and an analog-to-digital (A/D) converter that converts an analog signal to a digital signal. Further, the printer controller 2090 controls elements under instructions from a host device, and transfers the image data sent from the host device to the optical scanner 2010. Note that optimal developing conditions and transferring conditions for several brands of recording paper, which can be properly handled as a recording medium by the color printer 2000, are stored in the ROM as a "development and transfer table".

The photoreceptor drum 2030*a*, the charging device 2032*a*, the development roller 2033*a*, and the cleaning unit 2031*a* are used as a unit, and together configure an image forming station that forms a black image. Hereinafter, this image forming station may be referred to as a K-station.

The photoreceptor drum 2030*b*, the charging device 2032*b*, the development roller 2033*b*, and the cleaning unit 2031*b* are used as a unit, and together configure an image forming station that forms a cyan image. Hereinafter, this image forming station may be referred to as a C-station.

The photoreceptor drum 2030*c*, the charging device 2032*c*, the development roller 2033*c*, and the cleaning unit 2031*c* are used as a unit, and together configure an image forming station that forms a magenta image. Hereinafter, this image forming station may be referred to as an M-station.

The photoreceptor drum 2030*d*, the charging device 2032*d*, the development roller 2033*d*, and the cleaning unit 2031*d* are used as a unit, and together configure an image forming station that forms a yellow image. Hereinafter, this image forming station may be referred to as a Y-station.

A photosensitive layer is formed on the surface of each of the photoreceptor drums. The photoreceptor drums rotate in the direction of the arrows as illustrated in FIG. 1.

Each of the charging devices evenly charges the surface of the associated photoreceptor drum.

The optical scanner 2010 scans each of the surfaces of the electrically-charged photoreceptor drums, with the light that is modulated for each color based on the color image data (i.e., black image data, cyan image data, magenta image data, and yellow image data) received from the printer controller 2090. Accordingly, a latent image that corresponds to the image data of each color is formed on the surface of each of the photoreceptor drums. Note that the surface of each of the photoreceptor drums is scanned, and each of the photoreceptor drums carries an image. Each of the latent images moves towards the corresponding development roller as the photoreceptor drum rotates.

A toner form the corresponding toner cartridge is thinly and evenly applied to the surface of each of the development rollers as it rotates. Then, the toner applied to the surface of each of the development rollers moves and adheres to the portions of the surface of the corresponding photoreceptor drum that are irradiated with light by the optical scanner 2010. In other words, the development roller renders a latent image manifest by making the toner adhere to the latent image formed on the surface of the corresponding photoreceptor drum. Each of the toner images moves towards the transfer belt 2040 as the photoreceptor drum rotates.

Each of the toner images of yellow, magenta, cyan, and black is sequentially transferred to the transfer belt 2040 with specified timing. Then, the transferred toner images are superimposed on top of one another to form a color image.

The paper feed tray 2060 stores recording papers therein. The paper feed roller 2054 is arranged near the paper feed tray 2060, and the paper feed miler 2054 takes a piece of recording paper from the paper feed tray 2060. Then, the recording paper is fed between the transfer belt 2040 and the transfer roller 2042 with specified timing. Accordingly, the toner image on the transfer belt 2040 is transferred to the recording paper. The recording paper on which the toner image has been transferred is conveyed to the fixing device 2050.

At the fixing device 2050, heat and pressure are applied to the recording paper to fix the toner on the recording paper.

The recording paper on which the toner is fixed is conveyed to the paper output tray 2070 through the ejection roller 2058.

Each of the cleaning units 2031a to 2031d removes the residual toner left on the surface of the corresponding photoreceptor drum. The surface of the photoreceptor drum from which the residual toner has been removed moves back to a position where the surface of the photoreceptor drum faces the corresponding charging device.

The optical sensor 2245 is arranged in the conveyance path of recording paper taken from the paper feed tray 2060, and is used to determine the brand of the recording paper.

Figure 2:
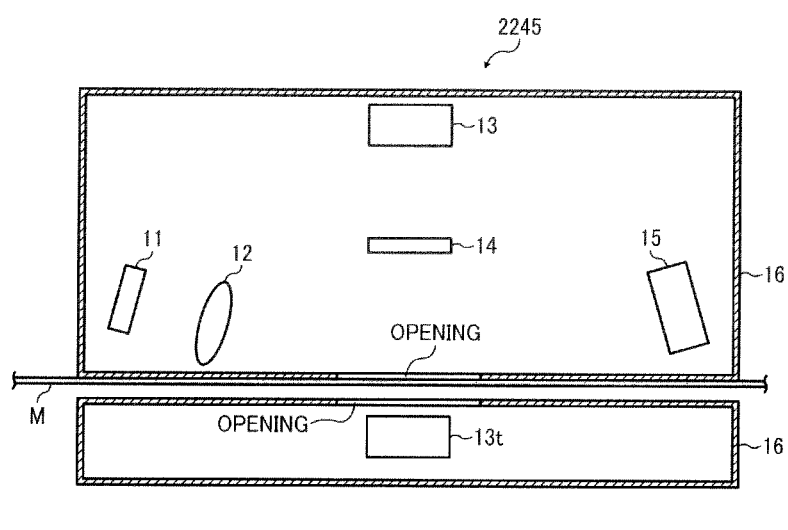
FIG. 2 illustrates the configuration of an optical sensor according to the first example embodiment of the present invention.

FIG. 2 illustrates the configuration of the optical sensor 2245 according to the present example embodiment of the present invention. As illustrated in FIG. 2, the optical sensor 2245 includes a light source 11, a collimate lens 12, three photosensors 13, 13t, and 15, a polarizing filter 14, and a dark box 16 that encloses these elements.

In the XYZ three-dimensional orthogonal coordinate system of FIG. 2, it is assumed that the direction orthogonal to the surface of recording paper M is a Z-axis direction.

The dark box 16 is a box made of metal such as aluminum, and the surface of the dark box 16 is anodized in black in order to reduce the influence of disturbance light and stray light.

The light source 11 includes a plurality of light-emitting units. Each of the light-emitting units is a vertical cavity-surface emitting laser (VCSEL) formed on the same substrate. In other words, the light source 11 includes a vertical cavity-surface emitting laser array (VCSEL array).

Figure 3:
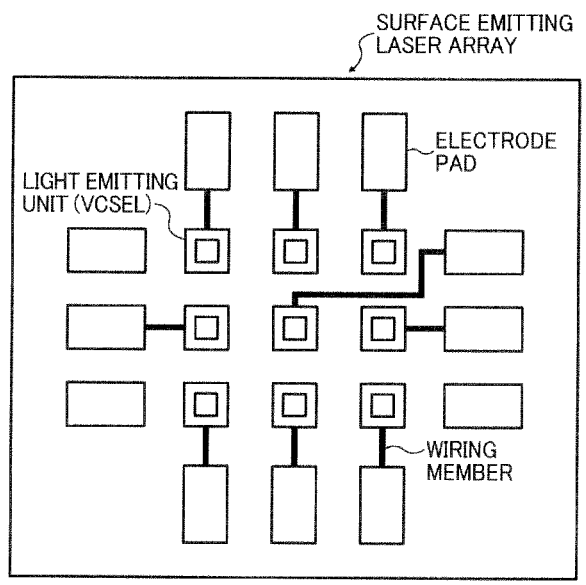
FIG. 3 illustrates a surface emitting laser array according to the first example embodiment of the present invention.

FIG. 3 illustrates an example of the VCSEL array in which nine light-emitting units (ch1 to ch9) are two-dimensionally arranged, according to the first example embodiment of the present invention. In FIG. 3, each of the VCSEL is connected to an electrode pad through a wiring member.

Figure 4:
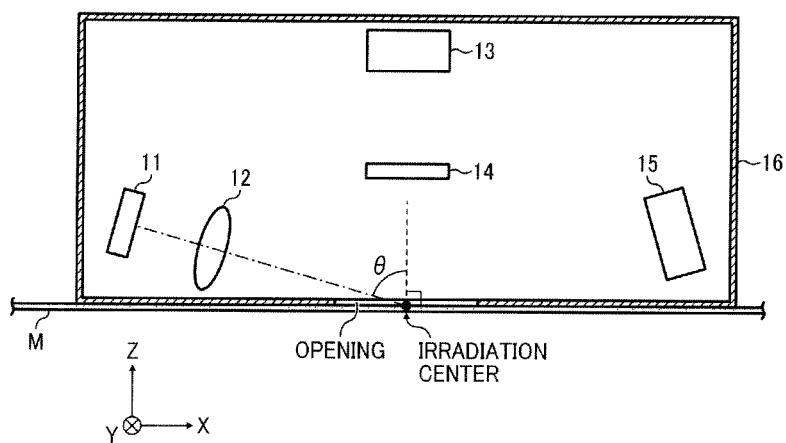
FIG. 4 illustrates the angle of incidence θ of irradiation light on recording paper, according to the first example embodiment of the present invention.

The light source 11 is arranged so as to irradiate the recording paper M with the s-polarized light FIG. 4 illustrates the angle of incidence θ of irradiation light on recording paper, according to the first example embodiment of the present invention. In the present example embodiment, the angle of incidence θ is 80°.

The collimate lens 12 is arranged on the optical path of the light flux emitted from the light source 11, and collimates the light flux. The light flux that has passed the collimate lens 12 passes through the opening of the dark box 16 to irradiate the recording paper M. Hereinafter, the center of the irradiated area on the surface of the recording paper M is referred to simply as an "irradiation center". Hereinafter, the light flux that has passed through the collimate lens 12 may be referred to as irradiation light.

Assuming that the light is incident on the boundary surface of a medium, the plane that includes the incident light beam and the normal line drawn from the point of incidence of the boundary surface is referred to as the incidence plane. When the incident light includes a plurality of light beams, an incidence plane exists for each of the light beams. However, for the purpose of simplification, the incidence plane of the light beam incident on the irradiation center is referred to as the incidence plane of the recording paper M. In other words, the plane that includes the irradiation center and is parallel with the XZ-plane is the incidence plane of the recording paper M.

In the present description, the terms "s-polarized light" and "p-polarized light" are used not only for the incident light on the recording paper M but also for the reflection light. This is for the purpose of simplification, and the light whose polarization direction is the same as that of the incident light (i.e., s-polarized light) on an incidence plane is referred to as the s-polarized light, and the light whose polarization direction is orthogonal to the s-polarized light is referred to as the p-polarized light. These terms are used with reference to the polarization direction of the incident light on the recording paper M.

The polarizing filter 14 is arranged on the +Z-side of the irradiation center. The polarizing filter 14 transmits p-polarized light and blocks s-polarized light. Alternatively, the polarizing filter 14 may be replaced with a polarization beam splitter whose capability is equivalent to that of the polarizing filter 14.

Figure 5:
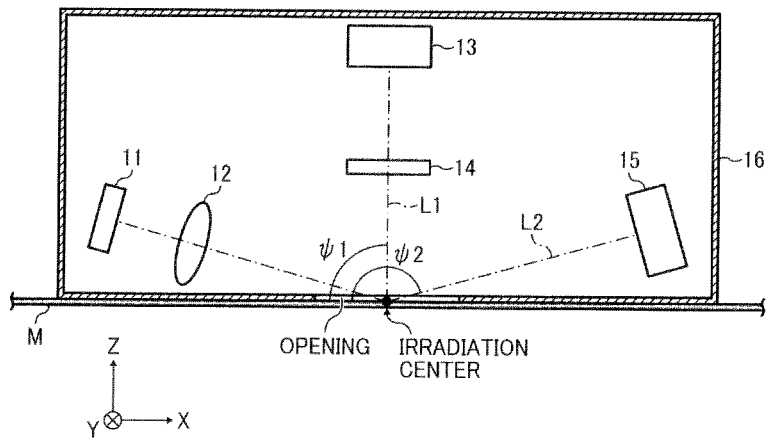
FIG. 5 illustrates the relative positions of a first photosensor and a second photosensor according to the first example embodiment of the present invention.

FIG. 5 illustrates the relative positions of the photosensor 13 and the photosensor 15 according to the present example embodiment. The photosensor 13 is arranged on the +Z-side of the polarizing filter 14. As illustrated in FIG. 5, the angle ψ1 which the surface of the recording paper M forms with a line L1, which is drawn through the irradiation center, the center of the polarizing filter 14, and the center of the photosensor 13, is 90 degrees.

The photosensor 15 is arranged on +X side of the irradiation center, with reference to the X-axis direction. As illustrated in FIG. 5, the angle ψ2 between the surface of the recording paper M and a line L2, which is drawn from the irradiation center to the center of the photosensor 15, is 170 degrees.

Note that the center of the light source 11, the irradiation center, the center of the polarizing filter 14, the center of the photosensor 13, and the center of the photosensor 15 are disposed on substantially the same plane.

Figure 6:
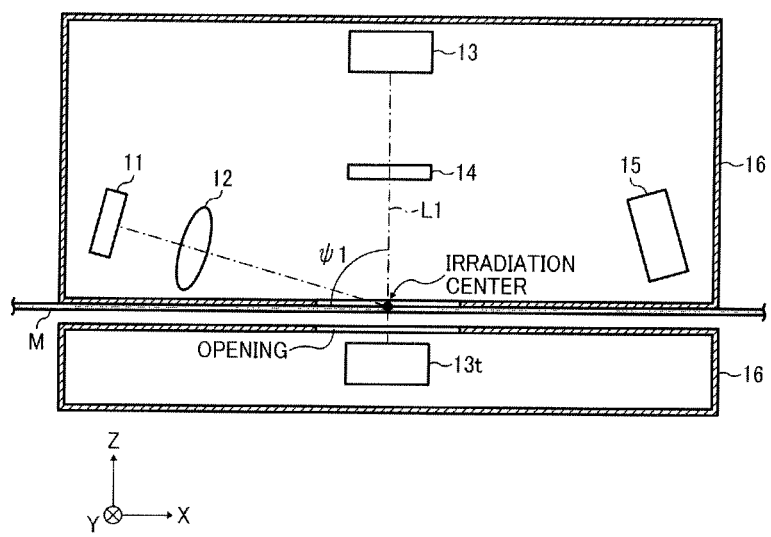
FIG. 6 illustrates the arrangement of a third photosensor according to the first example embodiment of the present invention.

FIG. 6 illustrates the arrangement of the photosensor 13t according to the present example embodiment. The photosensor 13t is arranged on the −Z-side of the recording paper M. As illustrated in FIG. 6, the center of the photosensor 13t is on the extension of the L1 to the −Z side of the recording medium M.

Figure 7A:
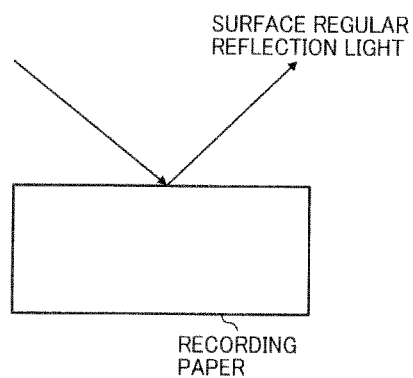
FIG. 7A illustrates surface regular reflection light.
Figure 7B:
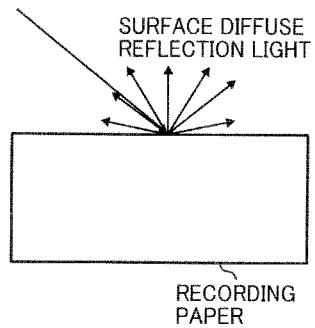
FIG. 7B illustrates surface diffuse reflection light.

The light reflected from recording paper when the recording paper is irradiated with light is classified into two kinds of reflected light, consisting of the light reflected at the surface of the recording paper, and the light reflected inside the recording paper. Moreover, the light reflected at the surface of the recording paper is classified into two kinds of reflected light, consisting of the light of regular reflection and the light of diffuse reflection. Hereinafter, the light reflected by regular reflection on the recording paper is referred to as "surface regular reflection light", and the light reflected by diffuse reflection is referred to as "surface diffuse reflection light" for the purpose of simplification, as illustrated in FIGS. 7A and 7B.

The surface of recording paper is composed of plane portions and oblique portions, and the smoothness of the recording paper is determined by the ratio of the plane portions to the oblique portions. The light reflected at a plane portion becomes surface regular reflection light, and the light reflected at an oblique portion becomes surface diffuse reflection light. The surface diffuse reflection light is completely-dispersed reflection light, and it is assumable that the direction of reflection is isotropic. When the smoothness is high, the light quantity of the surface regular reflection light increases accordingly.

Figure 7C:
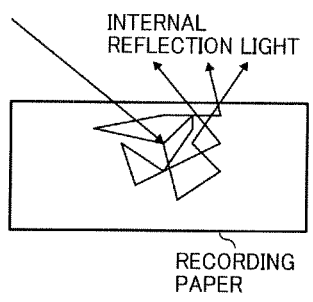
FIG. 7C illustrates internal reflection light.

When the recording paper is ordinary printing paper, the reflected light from the inside of the recording paper is composed of only diffuse reflection light because multiple scattering occurs inside the fibers of the recording paper. Hereinafter, the reflected light from the inside of the recording paper is referred to as "internal reflection light" for the purpose of simplification, as illustrated in FIG. 7C. The internal reflection light is also completely-dispersed reflection light in a similar manner to the surface diffuse reflection light, and it is assumable that the direction of reflection is isotropic.

Figure 7D:
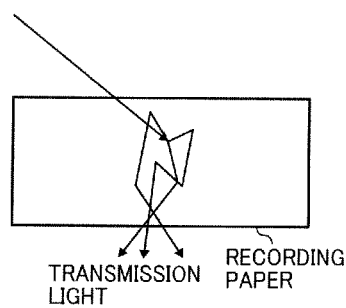
FIG. 7D illustrates transmission light.

FIG. 7D illustrates transmission light. When the recording paper is irradiated with light, there is not only reflected light but also transmission light that passes through the recording paper.

Figure 8:
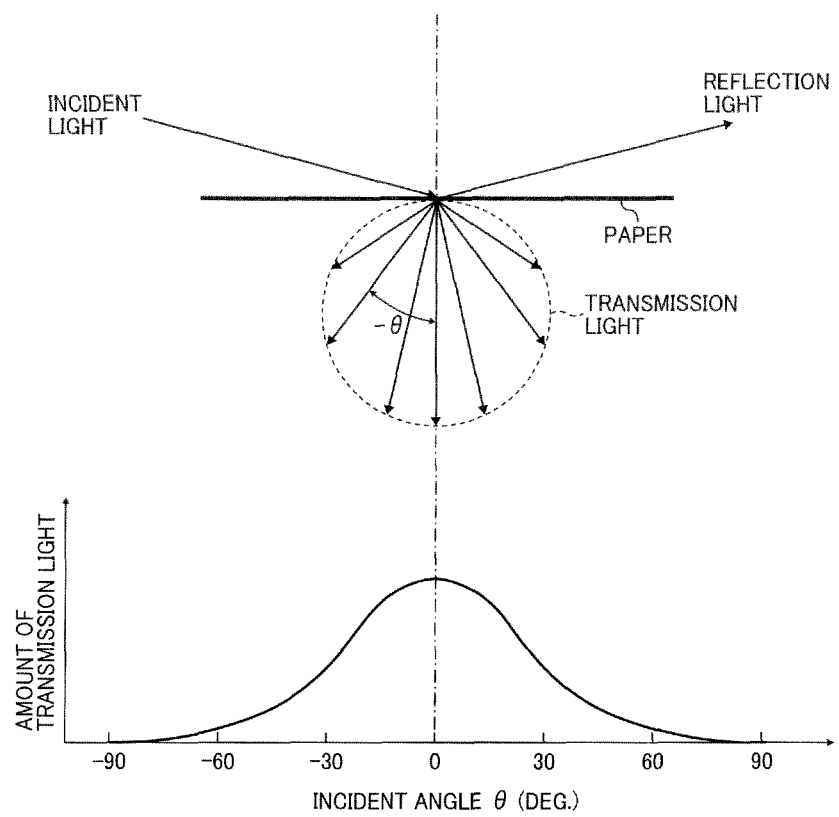
FIG. 8 illustrates the characteristics of transmission light according to an example embodiment of the present invention.

According to the experiments run by the inventor and his associates, it is known that the intensity distribution of the light that passes through the paper follows Lambert's Law. FIG. 8 illustrates the characteristics of transmission light according to the present example embodiment. The light that has entered the paper is dispersed by the fibers of the paper, and has an angle distribution that is not dependent on the angle of incidence, where the peak is at the light intensity of the direction orthogonal to the surface of the paper. For this reason, it is desired that the photosensor 15 be arranged directly underneath the irradiation center.

Figure 9:
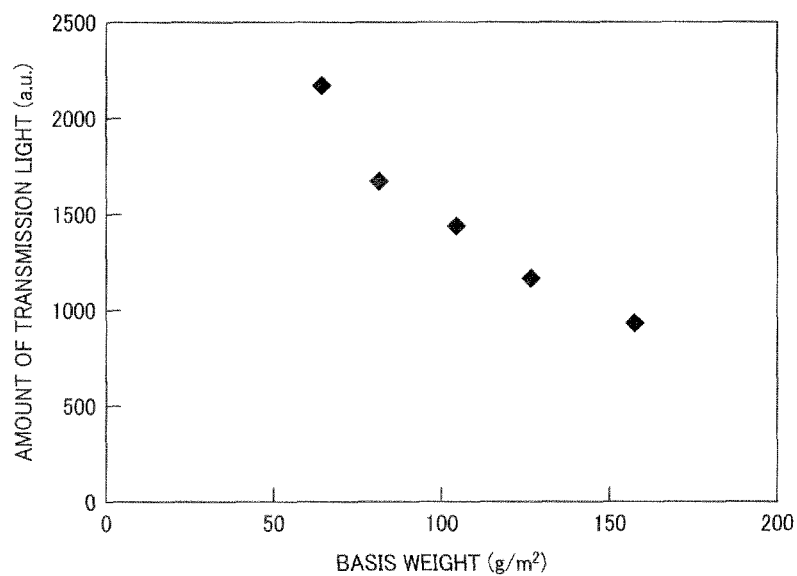
FIG. 9 illustrates the relationship between the amount of transmission light and the basis weight, according to an example embodiment of the present invention.

Because the light that passes through the paper is dispersed by the fibers of the paper, the amount of the transmission light decreases when the paper is thick, i.e., when the basis weight is greater. FIG. 9 illustrates experimental results indicating the relationship between the basis weight of paper and the amount of transmission light.

According to the present example embodiment, the identification accuracy of recording paper can be improved by measuring the amount of the transmission light in consideration of the basis weight of the recording paper, as described above.

The polarization direction of the surface regular reflection light and surface diffuse reflection light towards a photosensor is the same as the polarization direction of the incident light. Note that the polarization direction rotates on the surface of recording paper only when the incident light is reflected on a part of the surface that is inclined in the direction of the rotation with reference to the incident direction. Because the center of the light source, the irradiation center, and the centers of the photosensors are disposed on substantially the same plane in the present example embodiment, the light whose polarization direction is rotated on the surface of recording paper is not reflected to any of the photosensors.

By contrast, the polarization direction of the internal reflection light towards a photosensor is rotated with reference to the polarization direction of the incident light. This happens as the light that enters recording paper is transmitted through fibers and is subject to optical rotation while experiencing multiple scattering and the polarization direction is rotated.

Figure 10:
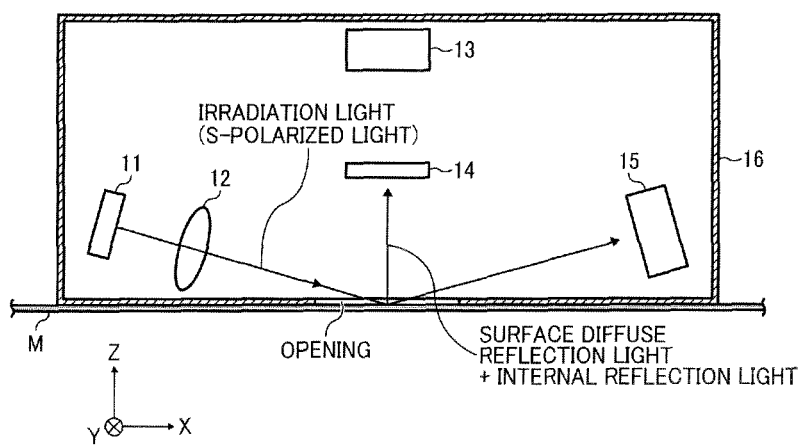
FIG. 10 illustrates the reflected light that enters a polarization filter, according to the first example embodiment of the present invention.

FIG. 10 illustrates the reflected light that enters the polarization filter 14, according to the present example embodiment. As illustrated in FIG. 10, reflection light including the surface diffuse reflection light and internal reflection light enters the polarizing filter 14.

As the surface diffuse reflection light that enters the polarizing filter 14 includes only the s-polarized light in a similar manner to the incident light, the surface diffuse reflection light that enters the polarizing filter 14 is all blocked at the polarizing filter 14. On the other hand, the internal reflection light includes both the s-polarized light and p-polarized light, and the p-polarized light of the internal reflection light passes through the polarizing filter 14. In other words, the p-polarized light included in the internal reflection light is received at the photosensor 13.

Figure 11:
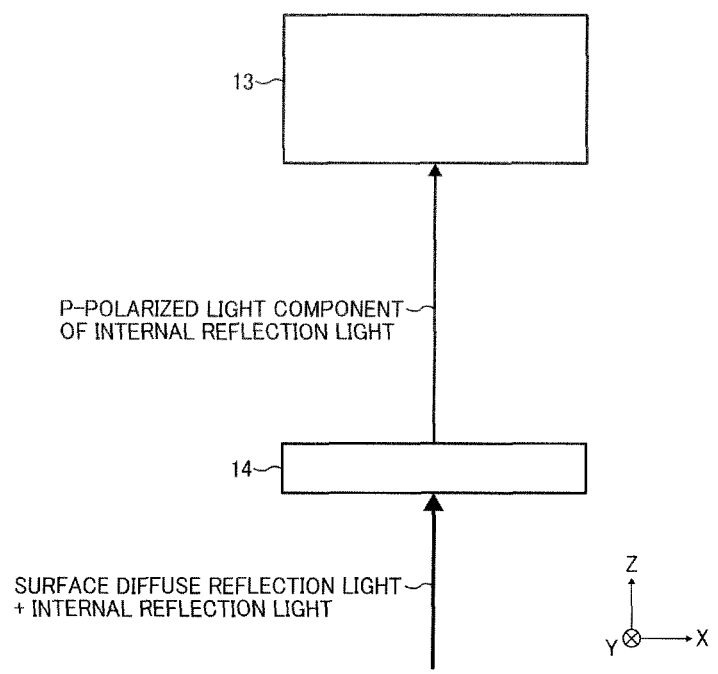
FIG. 11 illustrates the light received by the second photosensor, according to the first example embodiment of the present invention.

FIG. 11 illustrates the light received by the photosensor 13, according to the present example embodiment. Hereinafter, the p-polarized light included in the internal reflection light may be referred to as "p-polarized internal reflection light" for the purpose of simplification. In a similar manner, the s-polarized light included in the internal reflection light may be referred to as "s-polarized internal reflection light".

Figure 12:
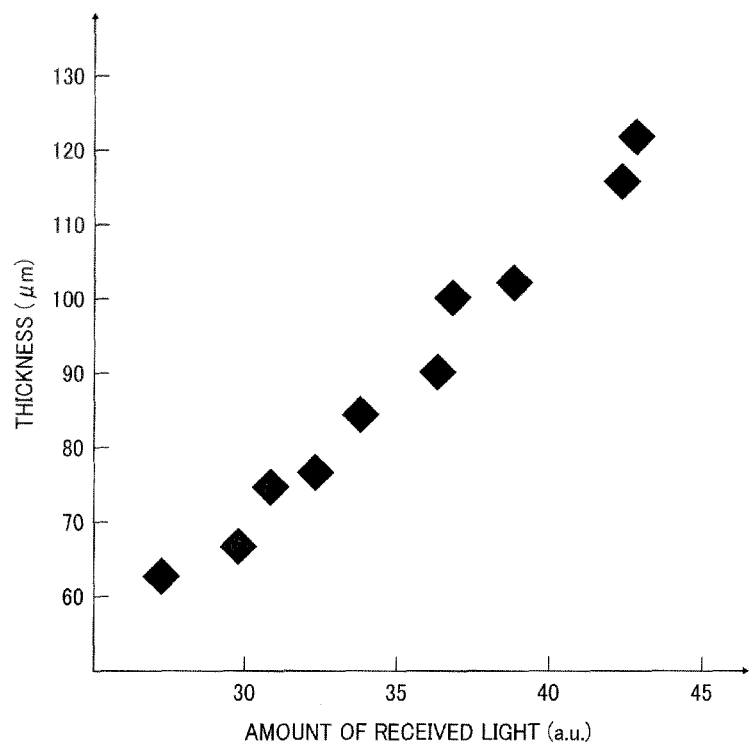
FIG. 12 illustrates the relationship between the thickness of recording paper and the amount of the light received by the second photosensor, according to an example embodiment of the present invention.
Figure 13:
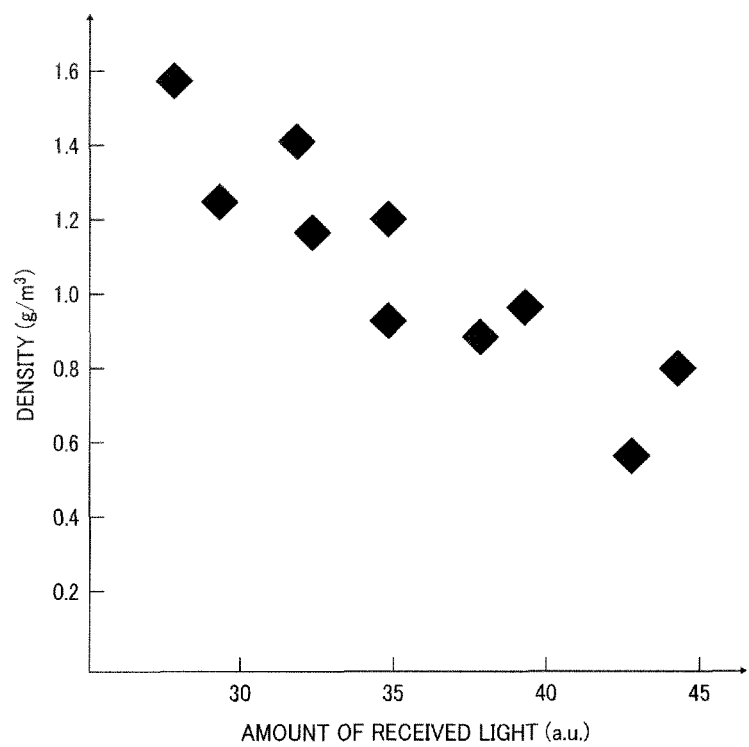
FIG. 13 illustrates the relationship between the density of recording paper and the amount of the light received by the second photosensor, according to an example embodiment of the present invention.

FIG. 12 illustrates the relationship between the thickness of recording paper and the amount of the light received by the photosensor 13, and FIG. 13 illustrates the relationship between the density of recording paper and the amount of the light received by the photosensor 13, according to the present example embodiment. According to the experiments run by the inventor and his associates, it is known that the amount of the p-polarized internal reflection light correlates with the thickness or density of recording paper. This is because the amount of the p-polarized internal reflection light is dependent upon the length of the path where the light passes through the fibers of the recording paper.

Figure 14:
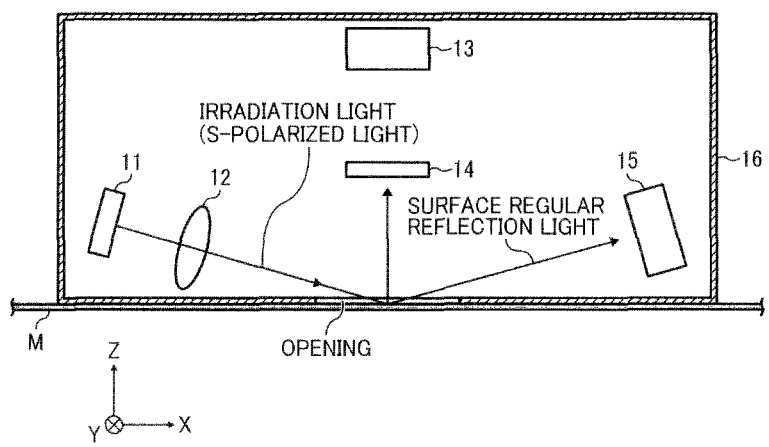
FIG. 14 illustrates the light received by the first photosensor, according to the first example embodiment of the present invention.

FIG. 14 illustrates the light received by the photosensor 15, according to the present example embodiment. As illustrated in FIG. 14, reflection light including the surface regular reflection light, surface diffuse reflection light, and internal reflection light enters the photosensor 15. At this light receiving position, the amount of the surface diffuse reflection light and internal reflection light is very small compared with the amount of the surface regular reflection light. For this reason, it can be assumed that the amount of the light received at the photosensor 15 is substantially equivalent to the amount of the surface regular reflection light.

Figure 15:
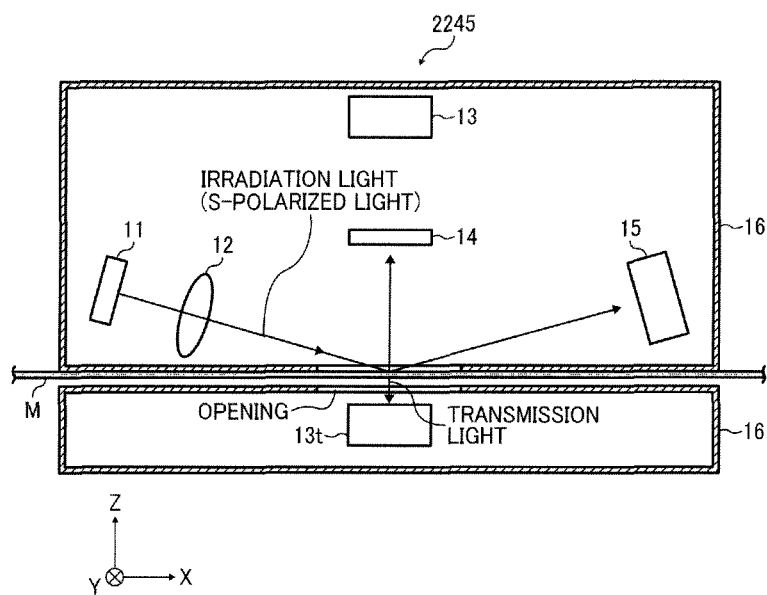
FIG. 15 illustrates the light received by the first photosensor, according to the first example embodiment of the present invention.

FIG. 15 illustrates the light received by the photosensor 13$t$, according to the first example embodiment of the present invention. As illustrated in FIG. 15, a part of the irradiation light that has passed through the recording paper M enters the photosensor 13$t$.

Each of the photosensors transmits an electrical signal to the printer controller 2090 based on the amount of the received light. Assuming that recording paper M is irradiated with the light flux emitted from the light source 11, the signal level of the signal output from the photosensor 13 is referred to as "S1". In a similar manner, the signal level of the signal output from the photosensor 15 is referred to as "S2", and the signal level of the signal output from the photosensor 13$t$ is referred to as "ST".

Figures 16, 17:
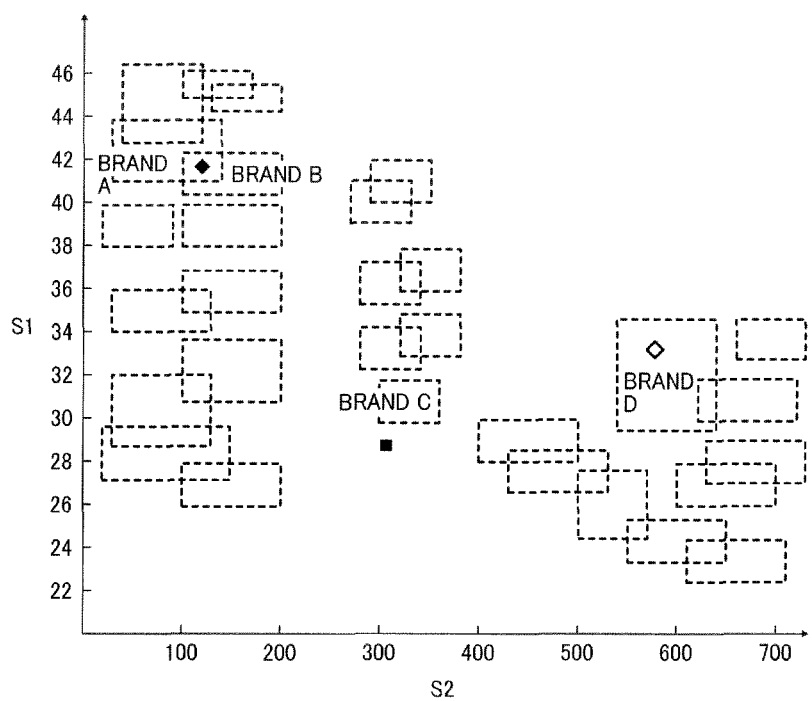
FIG. 16 illustrates a recording paper identification table according to the first example embodiment of the present invention.
FIG. 17 illustrates the relationship between S1 and S2 and the brands of recording paper, according to the first example embodiment of the present invention.

FIG. 16 illustrates a recording paper identification table according to the present example embodiment. In the present example embodiment, the values of S1, S2, and ST are measured for every brand of recording paper compatible with the color printer 2000 and the results are stored in the ROM of the printer controller 2090 as a recording paper identification table, in advance of shipment, for example, when adjustment processes are performed in the factory.

FIG. 17 illustrates the relationship between S1 and S2 and the brands of recording paper, according to the first example embodiment of the present invention. In FIG. 17, the measurement values of S1 and S2 are indicated for thirty brands of recording paper that are available in Japan. Each of the frames illustrated in FIG. 17 indicates a range of variation measured from the same brand. When the measurement values of only S1 and S2 are used as in FIG. 17, several ranges of variations, which correspond to a plurality of brands, overlap with each other. However, if the measurement values of ST are integrated into FIG. 17, such overlapping variations may be reduced or eliminated.

Next, processes in which the brand of recording paper taken from the paper feed tray 2060 is determined (i.e., brand determination processes) are described. The brand determination processes described below are performed by the printer controller 2090.

(1) A plurality of light-emitting units of the optical sensor 2245 are switched on at the same time.

(2) The values of S1, S2, and ST are obtained from the photosensors 13, 15, and 13*t*, respectively.

(3) The recording paper identification table is referred to, and the brand of the recording paper is determined based on the obtained values of S1, S2, and ST.

Figure 18:
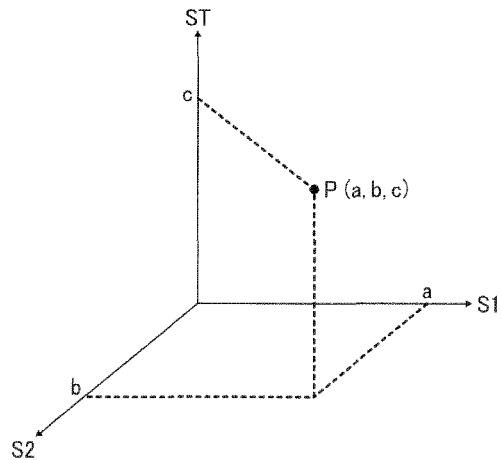
FIG. 18 illustrates three-dimensional coordinates related to a method of identifying the brand of recording paper, according to the first example embodiment of the present invention.

FIG. 18 illustrates three-dimensional coordinates related to a method of identifying the brand of recording paper, according to the first example embodiment of the present invention. As illustrated in FIG. 18, for example, three-dimensional coordinates with the axes of S1, S2, and ST are assumed. The recording paper identification table is referred to, and the brand whose range of variation includes, for example, coordinates P (a, b, c) are determined, where "a", "b", and "c" indicate the measurement values of S1, S2, and ST, respectively. For example, when the coordinates P (a, b, c) belongs to the range of variation of the Brand D only, the brand of the recording paper is determined to be D. For example, when the coordinates P (a, b, c) do not belong to the range of variation of any brand, the brand of the recording paper is determined to be the brand whose range of variation is closest to the coordinates P (a, b, c). For example, when the coordinates P (a, b, c) belong to the ranges of variation of both the Brand A and the Brand B, firstly, the difference between the mean values obtained for the Brand A and the measurement values (i.e., a, b, and c) as well as the difference between the mean values obtained for the Brand B and the measurement values (i.e., a, b, and c) are calculated. Then, the brand of the recording paper is determined to be the brand whose calculated difference is smaller than the other. Alternatively, the brand of the recording paper may be determined as follows. Firstly, it is assumed that the brand of the recording paper is the Brand A, and the variation of the Brand A is calculated again with the data to which the measurement values (i.e., a, b, and c) are added. Secondly, it is assumed that the brand of the recording paper is the Brand B, and the variation of the Brand B is calculated again with the data to which the measurement values (i.e., a, b, and c) are added. Then, the brand of the recording paper is determined to be the brand whose re-calculated variation is smaller than the other.

Alternatively, the brand of the recording paper may be determined as follows. Several candidate brands are determined based on the measurement values of S1 and S2, and these candidate brands are narrowed down to a single brand in consideration of the measurement value of ST.

(4) The brand identification process is terminated.

Then, the printer controller 2090 determines optimal developing conditions and transferring conditions by referring to a development and transfer table for the specified brand, and controls the development device and transfer device of each image forming station in accordance with the determined optimal developing conditions and transferring conditions. For example, the printer controller 2090 controls the transfer voltage or the amount of toner. Accordingly, a high-quality image is formed on recording paper.

Conventionally, the glossiness of the surface of recording paper is detected from the light quantity of the regular reflection, and the smoothness of the surface of the recording paper is detected from the ratio of the light quantity of the regular reflection to the light quantity of the diffuse reflection, in order to determine the type of the recording paper. By contrast, in the present example embodiment, not only the glossiness and smoothness of the surface of recording paper are detected but also other properties of the recording paper such as the thickness and density of the recording paper are detected from the reflection light and transmission light. Accordingly, the number of the identifiable types of recording paper is increased compared with the conventional technique.

For example, it was difficult in the conventional identification technique to distinguish plain paper from matte coated paper with only the information of the surface of recording paper used. In the present example embodiment, the information of the inside of the recording paper is also used in addition to the information of the surface of recording paper. Accordingly, it becomes possible to distinguish a number of brands of plain paper and a number of brands of matte coated paper in addition to the simple distinction between plain paper and matte coated paper. In other words, according to the first example embodiment, it becomes possible to determine the brand of object recording paper by detecting a difference in thickness and at least one of glossiness, smoothness, and density of the recording paper.

Moreover, the use of a surface emitting laser array makes it easy to adjust the irradiation light to parallel light rays, and contributes to the downsizing and cost reduction of an optical sensor.

It is known that the amount of the p-polarized light included in the internal reflection light is very small compared with the amount of the light with which the recording paper is irradiated (i.e., irradiation light quantity). For example, when the angle of incidence $\theta$ is 80 degrees, the light quantity of the diffuse reflection is smaller than the irradiation light quantity by four orders of magnitude, and the light quantity of the p-polarized light included in the internal reflection light is equal to or less than the light quantity of the diffuse reflection.

For this reason, in order to detect the p-polarized light included in the internal reflection light with precision, it is desired that the level of the output from a light source be set high and the p-polarized light included in the internal reflection light be received under conditions that maximize the precision of light detection and the amount of light detection.

In order to receive the p-polarized light included in the internal reflection light with the maximized precision and detection amount, the following matters are to be taken into consideration.

(1) The detection of the p-polarized light included in the internal reflection light is not performed in the direction where the surface regular reflection light is present.

This is because in actuality it is difficult to obtain only s-polarized light as irradiation light, and the light reflected at the surface tends to include p-polarized light. For this reason, if detection is performed in the direction where the surface regular reflection light is present, the p-polarized light that is originally included in the irradiation light and is reflected at the surface is usually greater than the p-polarized light included in the internal reflection light. Accordingly, if the polarizing filter 14 and the photosensor 13 are arranged in the direction where the surface regular reflection light is present, the amount of the reflection light cannot be precisely detected to obtain the information of the inside of the recording paper.

A polarizing filter with high extinction ratio may be used in order to obtain only s-polarized light as irradiation light, but the cost will increase in that case.

(2) The p-polarized light included in the internal reflection light is to be detected in the direction of the normal line drawn from the irradiation center of recording paper.

This is because the amount of reflection light in the detection direction follows the Lambert distribution as it can be assumed that the internal reflection light is complete diffuse reflection, and the amount of reflection light reaches a peak in the direction of the normal line drawn from the irradiation center. When the polarizng filter 14 and the photosensor 13 are arranged in the direction of the normal line drawn from the irradiation center, the signal-to-noise ratio (S/N) becomes high, and the best precision is achieved.

In addition to the reflection optical sensor, various kinds of other sensors may be installed to achieve a higher level of determination, such as a sensor that detects the thickness of a recording material by using transmission light or ultrasound, a sensor that detects the resistance value of a recording material, and a thermometer. However, the installation of such additional sensors will increase the number of the elements and lead to increased cost and upsizing of the whole apparatus.

As described above, the optical sensor 2245 according to the present embodiment includes, for example, the light source 11, the collimate lens 12, the three photosensors 13, 13t, and 15, the polarizing filter 14, and the dark box 16 that encloses these elements.

The photosensor 15 is arranged to mainly receive the surface regular reflection light, and the photosensor 13 is arranged to receive the p-polarized light included in the internal reflection light. The photosensor 13t is arranged to receive the light that has passed through the recording paper M.

The printer controller 2090 determines the brand of recording paper M based on the output signals of the photosensor 13, the photosensor 15, and the photosensor 13t.

As described above, the light quantity of the p-polarized light included in the internal reflection light is detected in the present example embodiment. Accordingly, it becomes possible to achieve precise separation of the internal reflection light. Conventionally, such separation of the light reflected from the inside of recording paper was difficult to achieve. Moreover, the amount of the light that has passed through the recording paper is detected in the present example embodiment. As the reflection light from the inside of the recording paper and the light that has passed through the recording paper include the information about the inside state of the recording paper, it becomes possible to improve the level of paper discrimination such that the level of the recording paper can be determined. Conventionally, such determination of brand was difficult.

Moreover, as various kinds of sensors are not combined and the configuration of parts is simple, it is possible to achieve a small optical sensor at low cost according to the present example embodiment.

Further, it becomes possible to identify the brand of recording paper more precisely than the conventional technique without increasing the cost and size of an optical sensor, according to the present example embodiment.

Because a surface emitting laser array is used as a light source, a polarizing filter is not required to adjust the irradiation light to linearly polarized light. Moreover, the use of a surface emitting laser array makes it easy to adjust the irradiation light to parallel light rays, and realizes a small light source that has a plurality of light-emitting units. Accordingly, downsizing and cost reduction of an optical sensor are realized.

Further, the use of a surface emitting laser array realizes high-density integration, which was difficult to achieve with the conventional LEDs or the like. Accordingly, all the laser light can be condensed to the optical axis of a collimate lens, and a plurality of rays of light flux can be collimated with a fixed angle of incidence. In other words, a collimate optical system can easily be realized.

Because the light source includes a plurality of light-emitting units, the light quantity of the p-polarized light included in the internal reflection light or the transmission light quantity can be increased by switching on all the light-emitting units at the same time.

The diffuse reflection light includes "the s-polarized light reflected at the surface" (A), "the s-polarized light reflected from the inside of recording paper" (B), and "the p-polarized light reflected from the inside of recording paper" (C). More precise paper discrimination may be achieved by using a polarizing filter to separate "the p-polarized light reflected from the inside of recording paper" (C) and detect the light quantity of the separated p-polarized light, but irradiation needs to be performed with greater amount of light for the following reasons.

When the irradiation light is the s-polarized light, the ratio of "the p-polarized light reflected from the inside of recording paper" (C) in the diffuse reflection light ((A)+(B)+(C)) is in the order of 40 percent at maximum. Because a low-cost polarizing filter, which is often provided for an ordinary sensor, has low transmittance, the light is attenuated by such a polarizing filter to 80 percent or so. For this reason, "the p-polarized light reflected from the inside of recording paper" (C) is attenuated when separated by a polarizing filter, and is substantially reduced to about 30 percent.

Conventionally, a sensor determines the type of recording paper from the selection of two to three types of recording paper (for example, the selection between coated paper and plastic sheet) based on the detected light quantity of the diffuse reflection light (A+B+C).

In the first example embodiment, the type of recording paper is selected from at least ten types of recording paper based only on "the p-polarized light reflected from the inside of recording paper" (C). In other words, at least five times more detailed paper discrimination is performed in the present example embodiment, compared with the conventional technique where only two types of recording paper can be identified. Accordingly, high resolution with smaller light quantity is desired in the present example embodiment compared with the conventional technique. If a photosensor with high resolution is used, determination can be made with small light quantity. However, the use of such a photosensor with high resolution leads to an increase in cost.

In the first example embodiment described above, high resolution is achieved by increasing the amount of irradiation light. More specifically, at least 3.3 times greater amount of irradiation light becomes necessary compared with the conventional technique because the amount of internal diffuse reflection light is substantially attenuated to about 30 percent as described above. Moreover, about 3.3*5 times greater amount of light becomes necessary in order to perform five times more detailed paper discrimination, compared with the conventional technique. As described above, the amount of irradiation light needs to be increased when a larger number of types of recording paper are to be identified.

When an unpolarized light source such as a light-emitting diode (LED) is used in the first example embodiment described above, the light from the light source needs to be filtered by a polarizing filter to obtain linearly polarized light (s-polarized light). When an inexpensive polarizing filter is used in this case, the amount of the light with which the recording paper is irradiated is attenuated to 40 percent of the amount of the light emitted from the LED (=50% (reduced amount of p-polarized light)*80% (amount attenuated by polarizing filter). Accordingly, when an LED is used as a light source, more than forty-times amount of irradiation light (=3.3*5/0.4) is necessary compared with the conventional technique.

However, the irradiation light quantity of a low-cost (LED) is a few W (typified by 1 mW), and it is difficult to achieve the irradiation light quantity of 40 to 50 mW or more. By contrast, it is easy for a surface emitting laser array to achieve desired irradiation light quantity by turning on a plurality of light-emitting units at the same time. In other words, it becomes possible to achieve desired irradiation light quantity by adopting a surface emitting laser array, so as to identify a larger number of types pf paper than the conventional technique.

Moreover, because the light source includes a plurality of light-emitting units, the contrast ratio of the speckle pattern of reflection light can be reduced by switching on all the light-emitting units at the same time, compared with cases in which only one light-emitting unit is switched on. Accordingly, the identification accuracy improves.

Further, more stable irradiation of linearly polarized light is achieved by adopting a surface emitting laser array. Accordingly, the light quantity of the p-polarized light included in the internal reflection light can be detected with precision.

Due to the provision of the optical sensor 2245, the color printer 2000 according to the present example embodiment can form a high-quality image without increasing the cost or size. Further, troublesome manual settings or failure in printing due to a setting error, which are still present in the conventional products, can be eliminated according to the present example embodiment.

Note that cases in which recording paper is irradiated with the s-polarized light have been described in the present example embodiment, but no limitation is indicated therein. In other words, recording paper may be irradiated with the p-polarized light. In such a case, however, a polarizing filter that transmits the s-polarized light is used in place of the polarizing filter 14.

Figure 19:
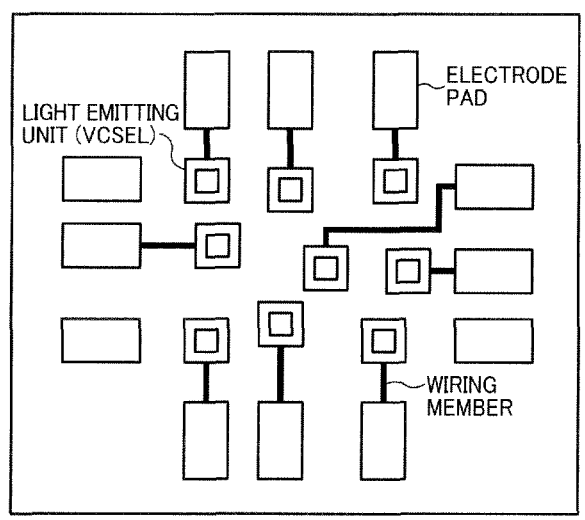
FIG. 19 illustrates a modification of a surface emitting laser array according to the first example embodiment of the present invention.

FIG. 19 illustrates a modification of a surface emitting laser array according to the first example embodiment of the present invention. As illustrated in FIG. 19, at least some of light-emitting units of a surface emitting laser array may be spaced differently from the other light-emitting units.

The number of the photosensors may be increased when an error is expected due to disturbance light or stray light.

Figure 20:
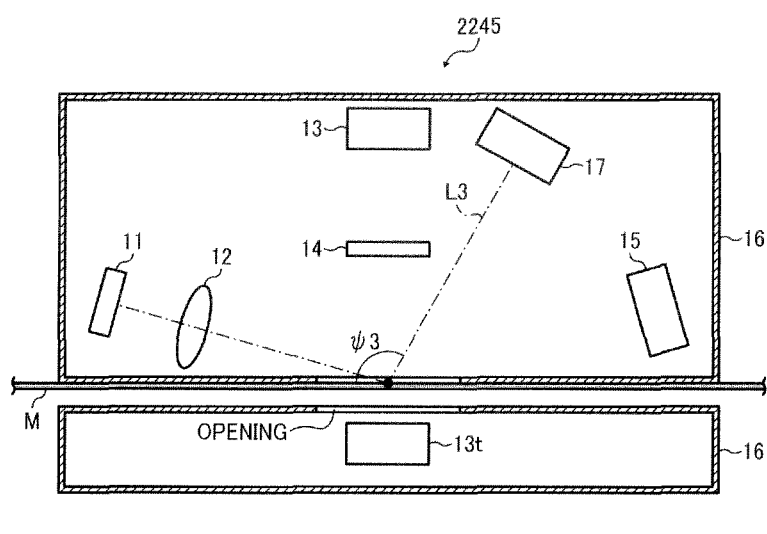
FIG. 20 illustrates a first modification of an optical sensor, according to the first example embodiment of the present invention.

FIG. 20 illustrates a first modification of an optical sensor, according to the first example embodiment of the present invention. As illustrated in FIG. 20, for example, the optical sensor 2245 may further include a photosensor 17. As illustrated in FIG. 20, reflection light including the surface diffuse reflection light and internal reflection light enters the photosensor 17. At this light receiving position, the amount of the internal reflection light is very small compared with the amount of the surface diffuse reflection light. For this reason, it can be assumed that the amount of the light received at the photosensor 17 is substantially equivalent to the amount of the surface diffuse reflection light.

As illustrated in FIG. 20, for example, the angle ψ3 between the surface of the recording paper M and a line L3, which is drawn from the irradiation center to the center of the photosensor 17, is 120 degrees. Note that the center of the light source 11, the irradiation center, the center of the polarizing filter 14, and the centers of the photosensors are disposed on substantially the same plane.

The paper-type discrimination processes performed by the printer controller 2090 in the case of the first modification are described as follows. Assuming that the recording paper M is irradiated with the light flux emitted from the light source 11, the signal level of the signal output from the photosensor 17 is referred to as "S4".

(1) A plurality of light-emitting units of the optical sensor 2245 are switched on at the same time.

(2) The values of S1, S2, ST, and S4 are calculated from the signals output from the photosensors.

(3) The value of S4/S2 is calculated.

(4) The recording paper identification table is referred to, and the brand of the recording paper is determined based on the calculated values of S1, ST, and S4/S2. Then, the paper-type discrimination process is terminated.

In the first modification of the first example embodiment illustrated in FIG. 20, the values of S1, ST, and S4/S2 are measured for every brand of recording paper compatible with the color printer 2000 and the results are stored in the ROM of the printer controller 2090 as a recording paper identification table, in advance of shipment, for example, when adjustment processes are performed in the factory.

Figure 21:
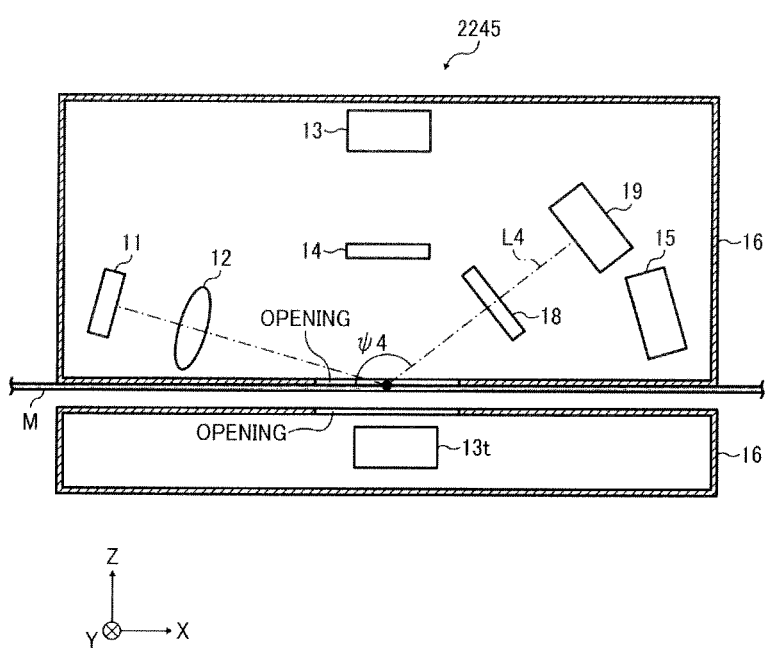
FIG. 21 illustrates a second modification of an optical sensor, according to the first example embodiment of the present invention.

FIG. 21 illustrates a second modification of an optical sensor, according to the first example embodiment of the present invention. As illustrated in FIG. 21, for example, the optical sensor 2245 may further include a polarizing filter 18 and a photosensor 19. As illustrated in FIG. 21, the polarizing filter 18 is arranged on the optical path of reflection light that includes the surface diffuse reflection light and the internal reflection light. The polarizing filter 18 transmits the p-polarized light and blocks the s-polarized light.

The photosensor 19 is arranged on the optical path of the light flux that has passed through the polarizing filter 18. The photosensor 19 receives the p-polarized light included in the internal reflection light.

As illustrated in FIG. 21, for example, the angle ψ4 between the surface of the recording paper M and a line L4, which is drawn from the irradiation center to the centers of the polarizing filter 18 and photosensor 19, is 150 degrees. Note that the center of the light source 11, the irradiation center, the centers of the polarizing filters, and the centers of the photosensors are disposed on substantially the same plane.

The paper-type discrimination processes performed by the printer controller 2090 in the case of the first modification according to the first example embodiment are described as follows. Assuming that the recording paper M is irradiated with the light flux emitted from the light source 11, the signal level of the signal output from the photosensor 19 is referred to as "S5".

(1) A plurality of light-emitting units of the optical sensor 2245 are switched on at the same time.

(2) The values of S1, S2, ST, and S5 are calculated from the signals output from the photosensors.

(3) The value of S5/S1 is calculated.

(4) The recording paper identification table is referred to, and the brand of the recording paper is determined based on the obtained values of S2, S5/S1, and ST. Then, the paper-type discrimination process is terminated.

In the second modification of the first example embodiment illustrated in FIG. 21, the values of S2, S5/S1, and ST are measured for every brand of recording paper compatible with the color printer 2000 and the results are stored in the ROM of the printer controller 2090 as a recording paper identification table, in advance of shipment, for example, when adjustment processes are performed in the factory.

Figure 22:
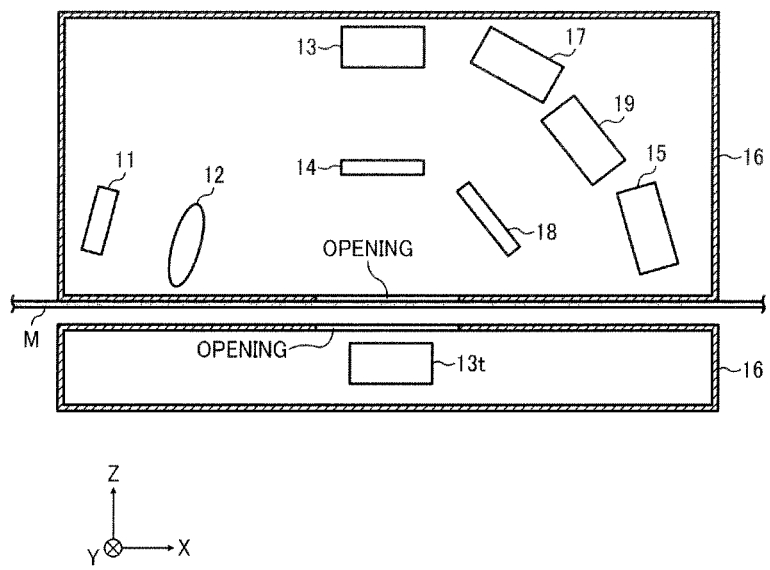
FIG. 22 illustrates a third modification of an optical sensor, according to the first example embodiment of the present invention.

FIG. 22 illustrates a third modification of an optical sensor, according to the first example embodiment of the present invention. As illustrated in FIG. 22, for example, the photosensor 17, the photosensor 19, and the polarizing filter 18 may further be provided.

The paper-type discrimination processes performed by the printer controller 2090 in the case of the first modification according to the first example embodiment are described as follows.

(1) A plurality of light-emitting units of the optical sensor 2245 are switched on at the same time.

(2) The values of S1, S2, ST, S4, and S5 are calculated from the signals output from the photosensors.

(3) The values of S5/S1 and S4/S2 are calculated.

(4) The recording paper identification table is referred to, and the brand of the recording paper is determined based on the obtained values of S5/S1, S4/S2, and ST. Then, the paper-type discrimination process is terminated.

Figure 23:
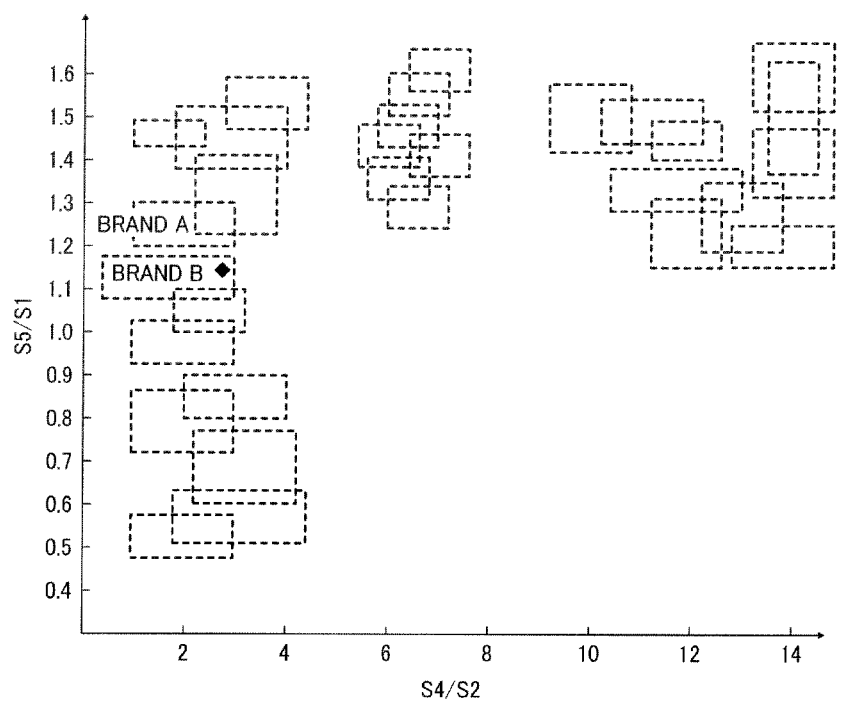
FIG. 23 illustrates the relationship between S5/S1 and S4/S2 and the brands of recording paper, according to the first example embodiment of the present invention.

In the third modification illustrated in FIG. 22, the values of S5/S1, S4/S2, and ST are measured for every brand of recording paper compatible with the color printer 2000 and the results are stored in the ROM of the printer controller 2090 as a recording paper identification table, in advance of shipment, for example, when adjustment processes are performed in the factory. FIG. 23 illustrates the relationship between S5/S1 and S4/S2 and the brands of recording paper, according to the first example embodiment of the present invention.

As described above, a plurality of photosensors are provided to detect the light diffused to several different directions, and the type of recording paper is determined based on the calculated values such as the ratio of the output values of the photosensors. Accordingly, precise determination becomes possible in spite of the existing disturbance light or stray light.

In the present modification, the printer controller 2090 may select several candidate brands of recording paper from the measurement values of S1, S2, S3, S4, S5, and ST, and these candidate brands can be narrowed down to a single brand in consideration of the values of S5/S1 and S4/S2.

In the third modification of the first example embodiment, S5/S1 is used for determination when the values of S1 and S5 are obtained. However, no limitation is indicated therein. In a similar manner, no limitation is indicated to the use of S4/S2 when the values of S2 and S4 are obtained.

In addition to the photosensor 17, the photosensor 19, and the polarizing filter 18 as described above, a photosensor that detects the amount of the surface diffuse reflection light in a similar manner to the photosensor 17 (this photosensor is referred to as a photosensor 22), a polarizing filter that is similar to the polarizing filter 18 (this photosensor is referred to as a polarizing filter 24), and a photosensor that receives the light that has passed the polarizing filter 24 (this photosensor is referred to as a photosensor 23) may further be provided. Here, the output levels of the photosensor 22 and the photosensor 23 are referred to as "S6" and "S7", respectively. In this case, paper-type discrimination may be performed by using the values of (S5/S1+S7/S1), (S4/S2+S6/S2), and ST. Moreover, paper-type discrimination may be performed by using the values of S5/S1, S7/S1, S4/S2, S6/S2, and ST. As a matter of course, a recording paper identification table is generated for the calculation of paper-type discrimination in advance of shipment, for example, when adjustment processes are performed in the factory, and is stored in the ROM of the printer controller 2090.

Figure 24:
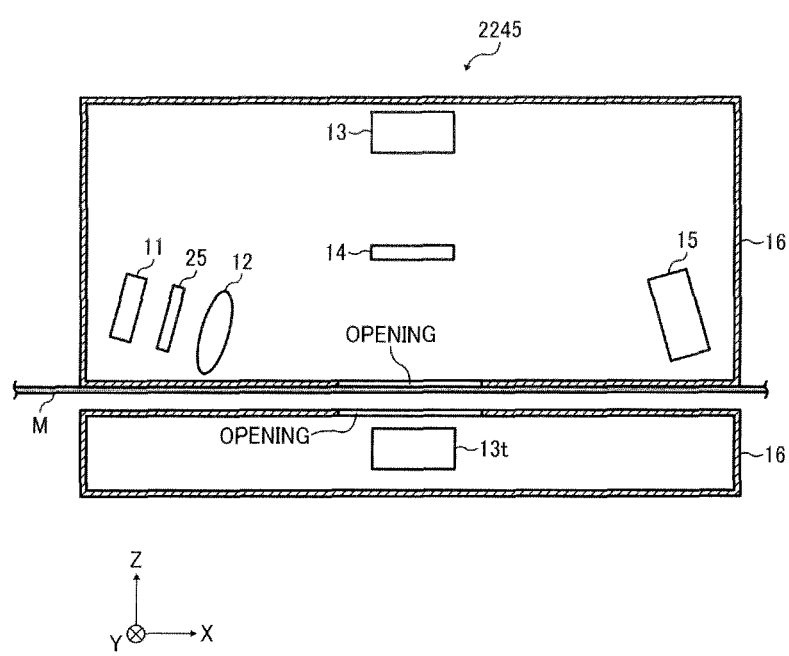
FIG. 24 illustrates Modification 4 of an optical sensor, according to the first example embodiment of the present invention.

In the present example embodiment, a conventional laser diode (LD) may be used in place of the surface emitting laser array. However, when a conventional LD is used, as illustrated in FIG. 24 as an example, a polarizing filter 25 needs to be arranged to obtain the s-polarized light from the irradiation light.

In the first example embodiment, a processing device may be added to the optical sensor such that the added processing device performs at least a part of the paper-type discrimination process performed by the printer controller 2090.

The optical sensor 2245 is applicable to an image forming apparatus that forms an image by ejecting ink onto recording paper.

Second Embodiment

Figure 25:
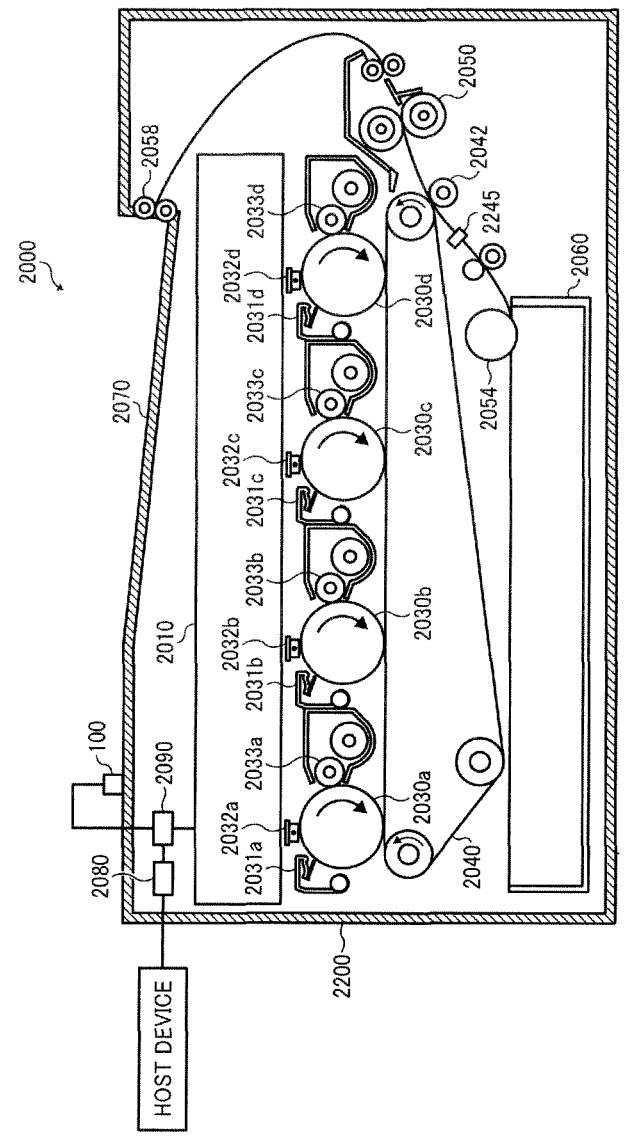
FIG. 25 is a schematic diagram the configuration of a color printer according to the second example embodiment of the present invention.

Next, the second example embodiment of the present invention is described with reference to FIGS. 25 to 31. FIG. 25 is a schematic diagram illustrating the configuration of the color printer 2000 according to the second example embodiment of the present invention.

The color printer 2000 according to the present example embodiment uses the sensor apparatus 100 in place of the optical sensor 2245, arranged near the operation panel outside the printer cabinet 2200, and is used to determine the brand of the recording paper. In regard to the other aspects of the configuration, the color printer 2000 according to the present example embodiment is equivalent to that of the first example embodiment described above. For this reason, the description concentrates on the differences from the first example embodiment. In the description of the second example embodiment, like reference signs are given to elements similar to those described in the first example embodiment, and the description of such similar elements are omitted.

Figure 26:
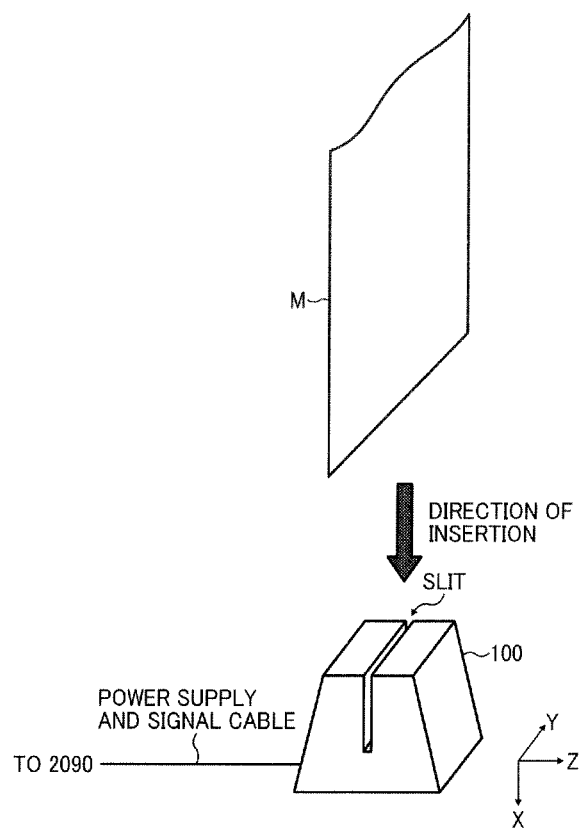
FIG. 26 is an external view of a sensor apparatus according to the second example embodiment of the present invention.

The sensor apparatus 100 is a stationary sensor apparatus. As illustrated in FIG. 26 as an example, the sensor apparatus 100 is shaped like a quadrangular pyramid, and has a slit of specified depth in the insertion direction of the recording paper M. In the XYZ three-dimensional orthogonal coordinate system according to the present example embodiment, it is assumed that the direction orthogonal to the surface of the recording paper M is the Z-axis direction, and that the direction in which the recording paper M is inserted into the slit is the +X direction.

Figure 27:
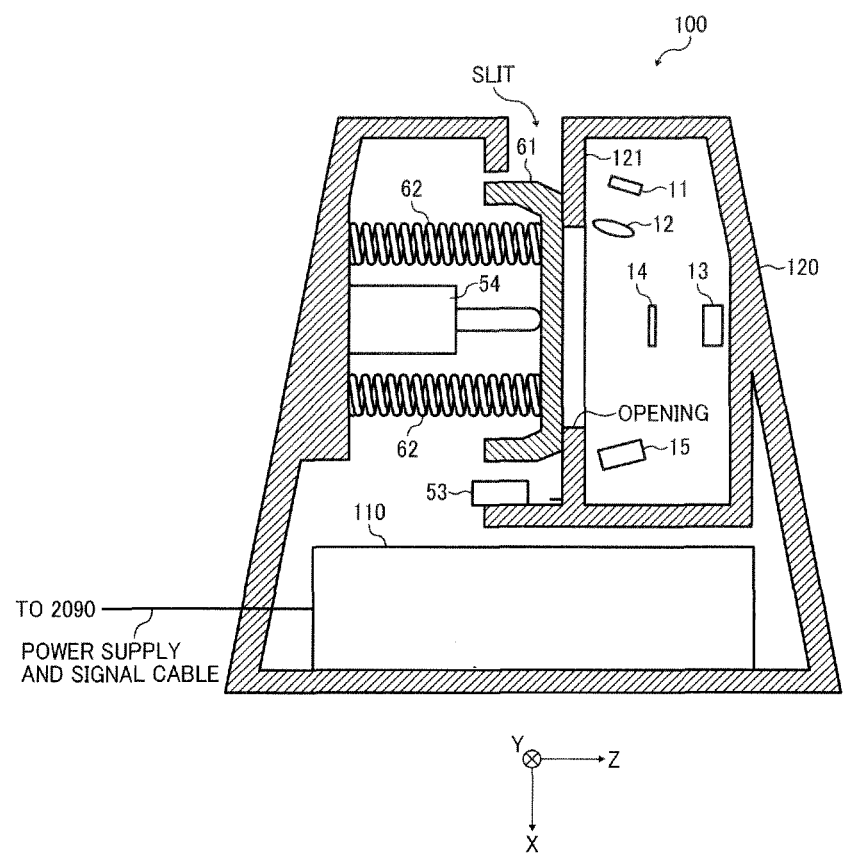
FIG. 27 illustrates the configuration of a sensor apparatus according to the second example embodiment of the present invention.

FIG. 27 illustrates the configuration of the sensor apparatus 100 according to the second example embodiment. As illustrated in FIG. 27, the sensor apparatus 100 includes, for example, the light source 11, the collimate lens 12, the two photosensors 13 and 15, the polarizing filter 14, a paper sensor 53, a displacement sensor 54, a pressing member 61, a plurality of spring members 62, a processing device 110, and a sensor cabinet 120. Note that the light source 11, the collimate lens 12, the two photosensors 13 and 15, the polarizing filter 14 of the sensor apparatus 100 form an optical sensor. In FIG. 27, the wall on the −Y side of the sensor cabinet 120 is removed for ease of illustration of the inner structure.

The sensor cabinet 120 includes an inner wall 121 that forms the wall on the +Z side of the slit. The optical sensor is enclosed in the sensor cabinet 120, and is placed on the +Z side of the inner wall 121. The inner wall 121 has an opening thereon.

The light flux that has passed through the collimate lens 12 passes the opening of the inner wall 121 to irradiate the recording paper M.

The pressing member 61 is arranged on the −Z side of the inner wall 121, and is attached to the sensor cabinet 120 through the spring members 62. When the recording paper M is not inserted into the slit, the +Z side surface of the pressing member 61 is in contact with the −Z side surface of the inner wall 121. The −Z side surface of the inner wall 121 serves as a reference plane when the thickness of the recording paper M is measured.

Figure 28:
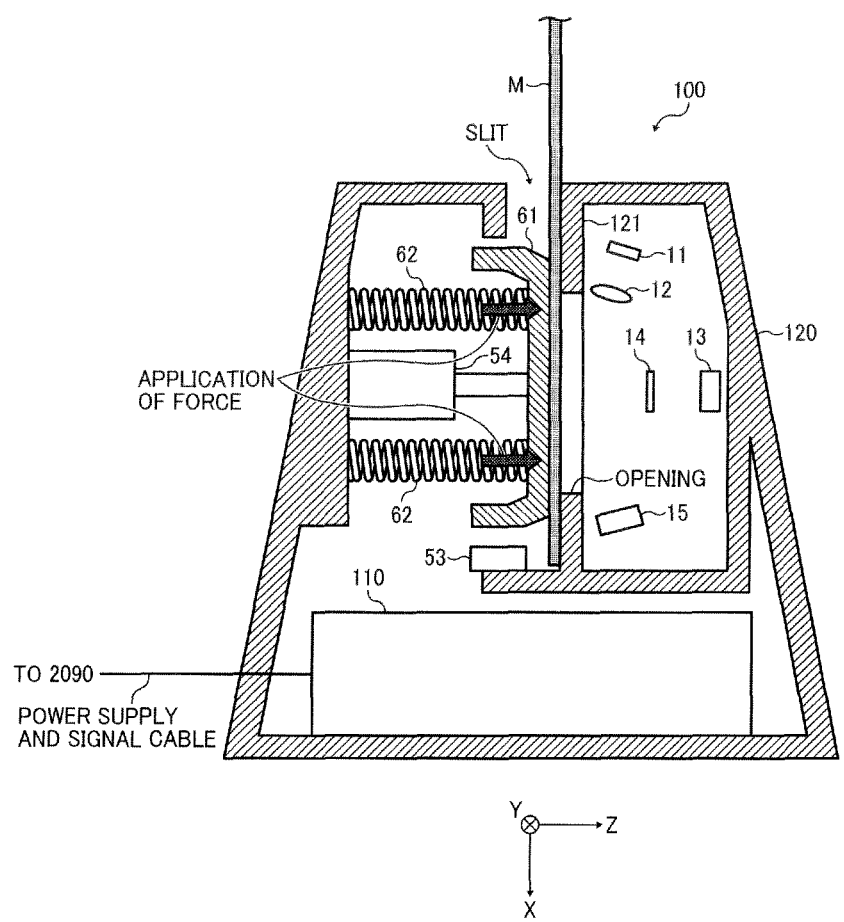
FIG. 28 illustrates the pressing force exerted on a pressing member, according to the second example embodiment of the present invention.

FIG. 28 illustrates the pressing force exerted on the pressing member 61, according to the second example embodiment. When the recording paper M is inserted into the slit, the pressing member 61 moves to the −Z side, and the recording paper M slides into the space between the inner wall 121 and the pressing member 61. When the pressing member 61 moves to the −Z side, the pressing force towards the +Z side is given to the pressing member 61 due to the resilience of the spring members 62. Accordingly, the recording paper M is pressed by the pressing member 61 against the inner wall 121. By so doing, the irradiation position or angle of incidence of the light is fixed with reference to the recording paper M, and the optical sensor can obtain a stable amount of reflection light. In other words, an improved precision is achieved in determining the brand of the recording paper M. If the recording paper M is not in intimate contact with the inner wall 121, the irradiation position or angle of incidence of the light fluctuates, and the brand of the recording paper M cannot be determined with precision.

Moreover, when the recording paper M is in full contact with the inner wall 121, a gap between the recording paper M and the optical sensor is minimized and the noise generated by disturbance light can be prevented. Further, the light (laser light) can be prevented from leaking to the outside of the sensor apparatus 100, and the safety for an operator is improved accordingly.

The intensity of the pressing force applied to the pressing member 61 by the spring members 62 is controlled such that the recording paper M can easily be pulled out from the slit. If the pressing force is too great, it becomes difficult to insert the recording paper M into the slit smoothly, and the recording paper M may be damaged when the recording paper M is pulled out from the slit. On the other hand, if the pressing force is too weak, a gap is created between the recording paper M and the inner wall 121, and the brand of the recording paper M may not be determined with precision.

The paper sensor 53 detects whether or not the recording paper M has reached a specified position (bottom) of the slit, and transmits to the processing device 110, for example, a high-level (H) signal when detected that the recording paper M has reached the specified position and a low-level (L) signal when detected that the recording paper M has not reached the specified position. A signal output from the paper sensor 53 serves as a timing signal used by the processing device 110 to determine the brand of the recording paper M.

The displacement sensor 54 is a cantilever displacement sensor, and transmits to the processing device 110 pulses whose number corresponds to the level of the displacement caused to the cantilever of the displacement sensor 54. In FIGS. 27 and 28, the tip of the cantilever is in contact with the −Z side surface of the pressing member 61. In this case, the displacement sensor 54 transmits to the processing device 110 pulses whose number corresponds to the amount of the movement of the pressing member 61 in the Z-axis direction. Hereinafter, the number of the pulses output from the displacement sensor 54 when the recording paper M is inserted into the slit is referred to as "St".

Figure 29:
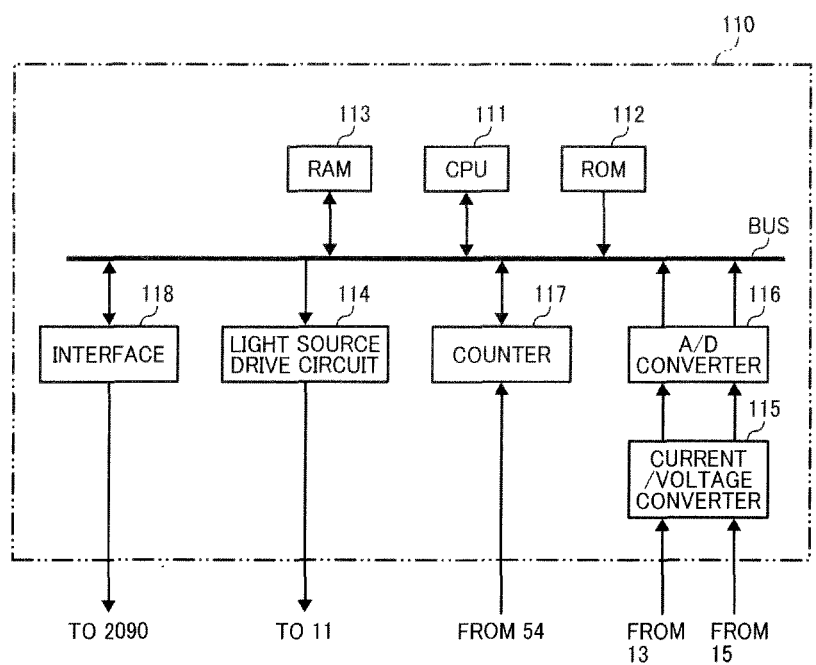
FIG. 29 is a block diagram illustrating the configuration of a processing device according to an example embodiment of the present invention.

FIG. 29 is a block diagram illustrating the configuration of the processing device 110 according to the second example embodiment. As illustrated in FIG. 29, the processing device 110 according to the second example embodiment of the present invention includes a CPU 111, a ROM 112, a RAM 113, a light source drive circuit 114, a current/voltage converter 115, an A/D converter 116, a counter 117, and an interface 118.

The power is supplied to the processing device 110 from the printer controller 2090 through a cable, and the processing device 110 performs bidirectional data communication with the printer controller 2090.

The ROM 112 stores a program described by codes readable by the CPU 111 and various kinds of data used for executing the program. The RAM 113 serves as a working memory.

The light source drive circuit 114 transmits a light-source driving signal to the light source 11 in accordance with the instructions provided by the CPU 111.

The current/voltage converter 115 converts the current signal output from the photosensors into a voltage signal. The A/D converter 116 converts the voltage signal output from the current/voltage converter 115 from an analog signal to a digital signal.

The counter 117 counts the number of the pulses output from the displacement sensor 54.

The interface 118 is a communication interface compatible with a universal serial bus (USB) or RS-232C, and controls the bidirectional data communication with the printer controller 2090.

The CPU 111 determines the brand of recording paper by using the program stored in the ROM 112. The printer controller 2090 is notified of the result of the determination.

In the present example embodiment, the values of S1, S2, and St are measured for every brand of recording paper compatible with the color printer 2000 and the results are stored in the ROM 112 as a recording paper identification table, in advance of shipment, for example, when adjustment processes are performed in the factory.

Figure 30:
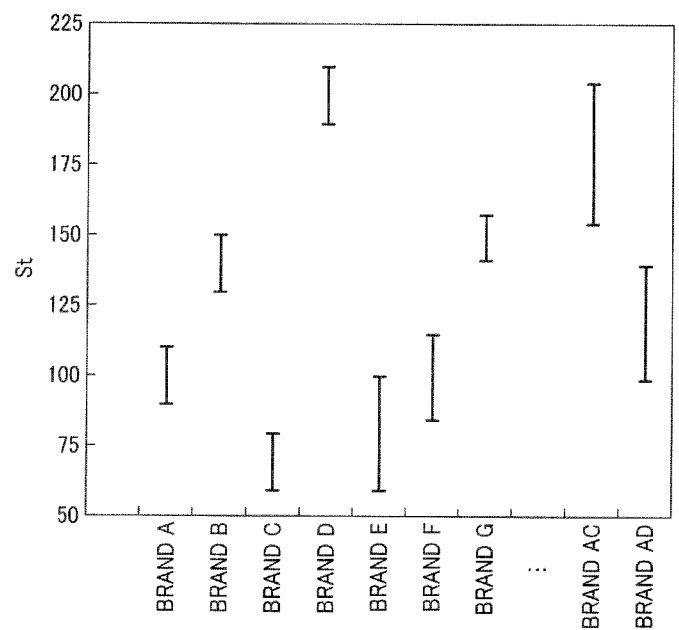
FIG. 30 depicts the values of St for each brand of recording paper, according to the second example embodiment of the present invention.

FIG. 30 depicts the relationship between brands and the values of St, according to the second example embodiment of the present invention.

When the measurement values of only S1 and S2 are used as in FIG. 17, several ranges of variations that correspond to a plurality of brands overlap with each other. However, if the measurement values of ST are integrated into FIG. 17, such overlapping portions may be reduced or eliminated.

Next, processes in which the brand of the recording paper M is determined (brand determination processes) are described.

Firstly, the operation performed by an operator in the brand determination processes are described.

1. The recording paper M is inserted into the slit of the sensor apparatus 100.

2. A request for a determination process is made through an operation panel. This request for a determination process is sent to the processing device 110 of the sensor apparatus 100 through the operation panel and the printer controller 2090.

3. After a specified period of time (for example, five seconds), the recording paper M is pulled out from the slit of the sensor apparatus 100.

Once the request for a determination process is received, the processing device 110 starts a brand determination process.

(1) The signal output from the paper sensor 53 is referred to, and when it is confirmed that the recording paper M is at a specified position, a plurality of light-emitting units of the light source 11 are switched on at the same time.

(2) The values of S1 and S2 are calculated from the signals output from the photosensors.

(3) The number of the pulses St output from the displacement sensor 54 is measured when the recording paper M is pulled out from the slit.

(4) The light-emitting units of the light source 11 are switched off.

(5) The recording paper identification table is referred to, and the brand of the recording paper is determined based on the obtained values of S1, S2, and St.

Figure 31:
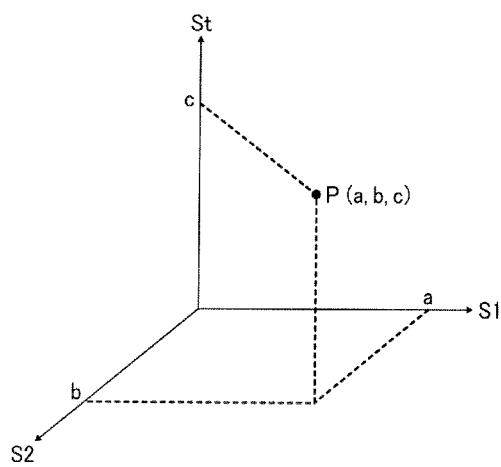
FIG. 31 illustrates three-dimensional coordinates related to a method of identifying the brand of recording paper, according to the second example embodiment of the present invention.

FIG. 31 illustrates three-dimensional coordinates related to a method of identifying the brand of recording paper, according to the second example embodiment. As illustrated in FIG. 31, for example, three-dimensional coordinates with the axes of S1, S2, and St are assumed. The recording paper identification table is referred to, and the brand whose range of variation includes, for example, coordinates P (a, b, c) are determined, where "a", "b", and "c" indicate the measurement values of S1, S2, and St, respectively. For example, when the coordinates P (a, b, c) belong to the range of variation of the Brand D only, the brand of the recording paper is determined to be the Brand D. For example, when the coordinates P (a, b, c) do not belong to the range of variation of any brand, the brand of the recording paper is determined to be the brand whose range of variation is closest to the coordinates P (a, b, c). For example, when the coordinates P (a, b, c) belong to the ranges of variation of both the Brand A and Brand B, firstly, the difference between the mean values obtained for the Brand A and the measurement values (i.e., a, b, and c) as well as the difference between the mean values obtained for the Brand B and the measurement values (i.e., a, b, and c) are calculated. Then, the brand of the recording paper is determined to be the brand whose calculated difference is smaller than any other.

Alternatively, the brand of the recording paper may be determined as follows. Firstly, it is assumed that the brand of the recording paper is the Brand A, and the variation of the Brand A is calculated again with the data to which the measurement values (i.e., a, b, and c) are added. Secondly, it is assumed that the brand of the recording paper is the Brand B, and the variation of the Brand B is calculated again with the data to which the measurement values (i.e., a, b, and c) are added. Then, the brand of the recording paper is determined to be the brand whose re-calculated variation is smaller than any other.

Alternatively, the brand of the recording paper may be determined as follows. Several candidate brands are determined based on the measurement values of S1 and S2, and these candidate brands are narrowed down to a single brand in consideration of the measurement value of St.

Further, the brand of the recording paper may be determined as follows. Several candidate brands are determined based on the measurement value of St, and these candidate brands are narrowed down to a single brand in consideration of the measurement values of S1 and S2.

(6) The printer controller 2090 is notified of the result of the determination. Then, the brand determination process is terminated.

The printer controller 2090 controls the display of the operation panel to display the determination results obtained from the processing device 110, and stores these determination results in the RAM of the printer controller 2090.

When the identified brand of the recording paper is displayed on the display of the operation panel, an operator sets the recording paper of the specified brand to the paper feed tray 2060. The brand of the recording paper displayed on the display of the operation panel may be registered into the printer controller 2090 by using the keys on the operation panel.

Then, the printer controller 2090 reads the brand of the recording paper from the RAM when a request for a print job is received, and then determines optimal developing conditions and transferring conditions from the development and transfer table for the specified brand of the recording paper.

Then, the printer controller 2090 controls the development device and transfer device of each image forming station in accordance with the determined optimal developing conditions and transferring conditions. For example, the printer controller 2090 controls the transfer voltage or the amount of toner. Accordingly, a high-quality image is formed on recording paper.

Conventionally, the glossiness of the surface of recording paper is detected from the light quantity of the regular reflection, and the smoothness of the surface of the recording paper is detected from the ratio of the light quantity of the regular reflection to the light quantity of the diffuse reflection, in order to determine the type of the recording paper. By contrast, in the second example embodiment, not only the glossiness and smoothness of the surface of recording paper are detected by an optical sensor but also other properties of the recording paper such as the thickness and density of the recording paper are detected from the diffuse reflection light from the inside of the recording paper. Accordingly, the number of the identifiable types of recording paper is increased compared with the conventional technique, and identification accuracy is improved by using a thickness sensor to more precisely detect the thickness of the recording paper.

For example, it was difficult to distinguish plain paper from matte coated paper with only the information of the surface of recording paper used in the conventional identification technique. In the second example embodiment, the information of the inside of recording paper is also used in addition to the information of the surface of recording paper. Accordingly, it becomes possible to distinguish a number of brands of plain paper and a number of brands of matte coated paper in addition to the simple distinction between plain paper and matte coated paper. Further, the thickness information of the recording paper is added, and it becomes possible to more precisely distinguish a number of brands of plain paper and a number of brands of matte coated paper. In other words, according to the second example embodiment, it becomes possible to determine the brand of object recording paper by detecting a difference in thickness and at least one of glossiness, smoothness, and density of the recording paper.

As described above, the sensor apparatus 100 according to the second example embodiment includes, for example, the light source 11, the collimate lens 12, the photosensors 13 and 15, the polarizing filter 14, the paper sensor 53, the displacement sensor 54, the pressing member 61, the spring members 62, the processing device 110, and sensor cabinet 120. Note that the light source 11, the collimate lens 12, the photosensors 13 and 15, the polarizing filter 14 of the sensor apparatus 100 form an optical sensor.

The light source 11 and the collimate lens 12 form an irradiation system, and the irradiation system emits the s-polarized light to recording paper in a direction oblique to the z-axis direction. The photosensor 15 is arranged on the optical path of the light that is emitted from the irradiation system and then is reflected at the recording paper by regular reflection (surface regular reflection light). The polarizing filter 14 and the photosensor 13 are arranged on the optical path of the light that is reflected by diffuse reflection in the direction of the normal line drawn from the surface of the recording paper. The polarizing filter 14 transmits the p-polarized light, and the photosensor 13 receives the light that has passed through the polarizing filter 14 (i.e., the p-polarized light included in the internal reflection light). The displacement sensor 54 detects the thickness of the recording paper via the pressing member 61. The optical sensor is arranged opposite the displacement sensor 54 across the recording paper.

The processing device 110 determines the brand of recording paper based on the signals output from the photosensors and the signal output from the displacement sensor 54.

As described above, the light quantity of the p-polarized light included in the internal reflection light is detected. Accordingly, it becomes possible to achieve precise separation of the internal reflection light. Conventionally, such separation of the light reflected from the inside of recording paper was difficult to achieve. The reflection light from the inside of recording paper includes the information about the inside state of the recording paper, and thus it becomes possible to improve the level of paper discrimination such that the level of the recording paper can be determined. Conventionally, such determination of brand was difficult. Moreover, the thickness of recording paper is detected, and this also contributes to the improvement of discrimination accuracy.

Accordingly, the processing device 110 can identify the type of recording paper more precisely than the conventional technique.

Moreover, as the light source 11 has a surface emitting laser array, it becomes possible to reduce the size and cost of the sensor apparatus 100.

Due to the provision of the sensor apparatus 100, the color printer 2000 according to the second example embodiment can form a high-quality image. Further, troublesome manual settings or failure in printing due to a setting error, which are still present in the conventional products, can be eliminated in the present example embodiment.

The number of the photosensors may be increased when an error is expected due to disturbance light or stray light.

Figure 32:
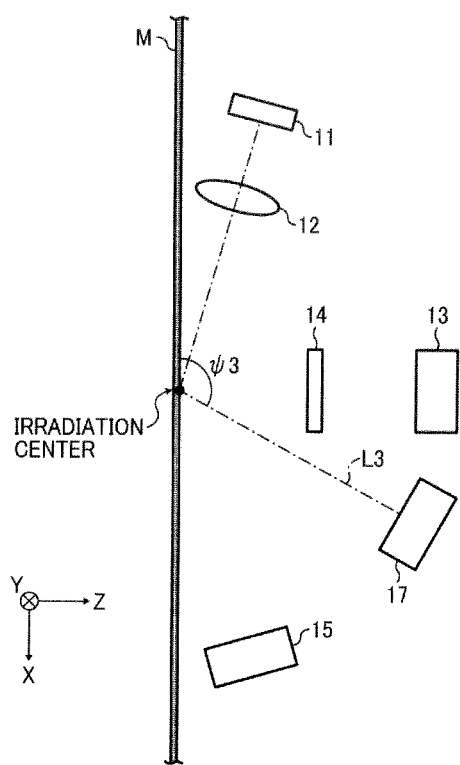
FIG. 32 illustrates a first modification of an optical sensor, according to the second example embodiment of the present invention.

FIG. 32 illustrates a first modification of an optical sensor, according to the second example embodiment of the present invention. As illustrated in FIG. 32, for example, the optical sensor 2245 may further include the photosensor 17. As illustrated in FIG. 32, reflection light including the surface diffuse reflection light and internal reflection light enters the photosensor 17. At this light receiving position, the amount of the internal reflection light is very small compared with the amount of the surface diffuse reflection light. For this reason, it can be assumed that the amount of the light received at the photosensor 17 is substantially equivalent to the amount of the surface diffuse reflection light.

As illustrated in FIG. 32, for example, the angle $\psi 3$ between the surface of the recording paper M and a line L3, which is drawn from the irradiation center to the center of the photosensor 17, is 120 degrees. Note that the center of the light source 11, the irradiation center, the center of the polarizing filter 14, and the centers of the photosensors are disposed on substantially the same plane.

The brand determination processes performed by the processing device 110 in the case of the first modification according to the second example embodiment are described as follows. Assuming that the recoding paper M is irradiated with the light flux emitted from the light source 11, the signal level of the signal output from the photosensor 17 is referred to as "S3".

(1) The signal output from the paper sensor 53 is referred to, and when it is confirmed that the recording paper M is at a specified position, a plurality of light-emitting units of the light source 11 are switched on at the same time.

(2) The values of S1, S2, and S3 are calculated from the signals output from the photosensors.

(3) The number of the pulses St output from the displacement sensor 54 is measured when the recording paper M is pulled out from the slit.

(4) The light-emitting units of the light source 11 are switched off.

(5) The value of S3/S2 is calculated.

(6) The recording paper identification table is referred to, and the brand of the recording paper is determined based on the obtained values of S1, S3/S2, and St.

(7) The printer controller 2090 is notified of the result of the determination. Then, the brand determination process is terminated.

In the first modification of the second example embodiment illustrated in FIG. 32, the values of S1, S3/S2, and St are measured for every brand of recording paper compatible with the color printer 2000 and the results are stored in the ROM 112 of the processing device 110 as a recording paper identification table, in advance of shipment, for example, when adjustment processes are performed in the factory.

Figure 33:
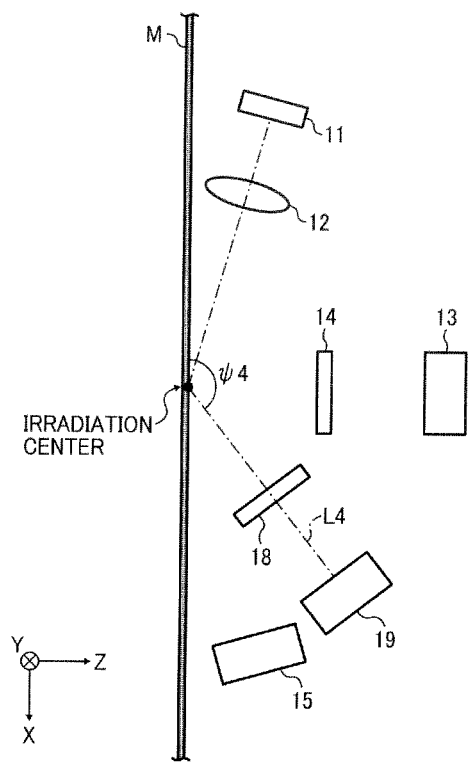
FIG. 33 illustrates a second modification of an optical sensor, according to the second example embodiment of the present invention.

FIG. 33 illustrates a second modification of an optical sensor, according to the second example embodiment of the present invention. As illustrated in FIG. 33, for example, the optical sensor 2245 may further include the polarizing filter 18 and the photosensor 19. As illustrated in FIG. 33, the polarizing filter 18 is arranged on the optical path of the reflection light that includes the surface diffuse reflection light and internal reflection light. The polarizing filter 18 transmits the p-polarized light and blocks the s-polarized light.

The photosensor 19 is arranged on the optical path of the light flux that has passed through the polarizing filter 18. The photosensor 19 receives the p-polarized light included in the internal reflection light.

As illustrated in FIG. 33, for example, the angle $\psi 4$ between the surface of the recording paper M and a line L4, which is drawn from the irradiation center to the centers of the polarizing filter 18 and photosensor 19, is 150 degrees. Note that the center of the light source 11, the irradiation center, the centers of the polarizing filters, and the centers of the photosensors are disposed on substantially the same plane.

The brand determination processes performed by the processing device 110 in the case of the second modification according to the second example embodiment are described as follows. Assuming that the recording paper M is irradiated with the light flux emitted from the light source 11, the signal level of the signal output from the photosensor 19 is referred to as "S4".

(1) The signal output from the paper sensor 53 is referred to, and when it is confirmed that the recording paper M is at a specified position, a plurality of light-emitting units of the light source 11 are switched on at the same time.

(2) The values of S1, S2, and S4 are calculated from the signals output from the photosensors.

(3) The number of the pulses St output from the displacement sensor 54 is measured when the recording paper M is pulled out from the slit.

(4) The light-emitting units of the light source 11 are switched off.

(5) The value of S4/Sa is calculated.

(6) The recording paper identification table is referred to, and the brand of the recording paper is determined based on the obtained values of S4/S1, S2, and St.

(7) The printer controller 2090 is notified of the result of the determination. Then, the brand determination process is terminated.

In the second modification of the second example embodiment illustrated in FIG. 33, the values of S4/S1, S2, and St are measured for every brand of recording paper compatible with the color printer 2000 and the results are stored in the ROM 112 of the processing device 110 as a recording paper identification table, in advance of shipment, for example, when adjustment processes are performed in the factory.

Figure 34:
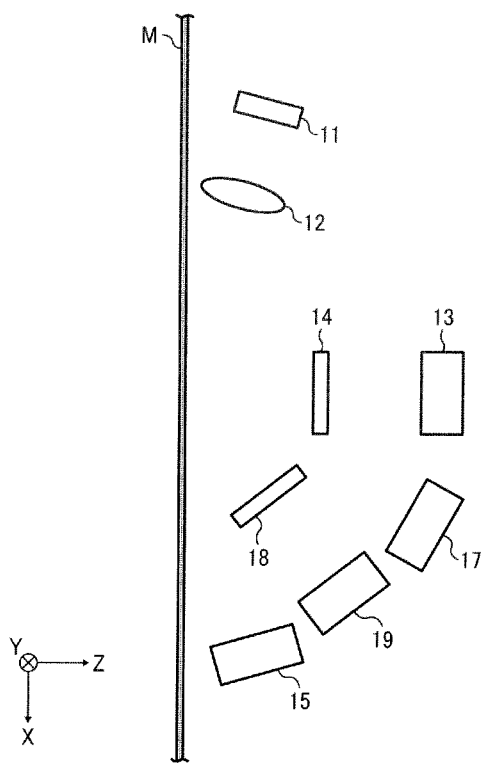
FIG. 34 illustrates a third modification of an optical sensor, according to the second example embodiment of the present invention.

FIG. 34 illustrates a third modification of an optical sensor, according to the second example embodiment of the present invention. As illustrated in FIG. 34, for example, the photosensor 17, the photosensor 19, and the polarizing filter 18 may further be provided.

The brand determination processes performed by the processing device 110 in the case of the third modification according to the second example embodiment are described as follows.

(1) The signal output from the paper sensor 53 is referred to, and when it is confirmed that the recording paper M is at a specified position, a plurality of light-emitting units of the light source 11 are switched on at the same time.

(2) The values of S1, S2, S3, and S4 are calculated from the signals output from the photosensors.

(3) The number of the pulses St output from the displacement sensor 54 is measured when the recording paper M is pulled out from the slit.

(4) The light-emitting units of the light source 11 are switched off.

(5) The values of S4/S1 and S3/S2 are calculated.

(6) The recording paper identification table is referred to, and the brand of the recording paper is determined based on the obtained values of S4/S1, S3/S2, and St.

(7) The printer controller 2090 is notified of the result of the determination. Then, the brand determination process is terminated.

Figure 35:
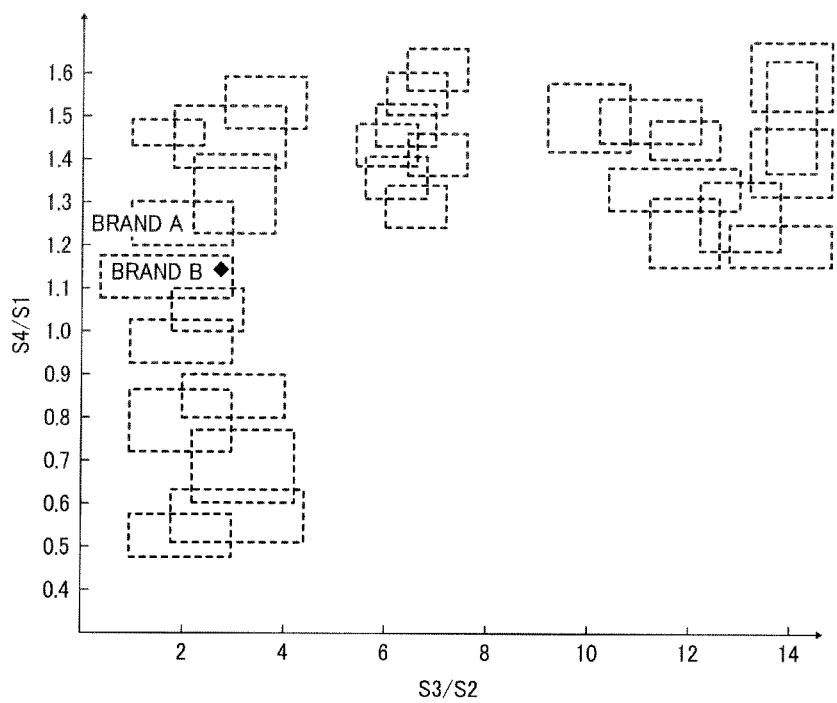
FIG. 35 illustrates the relationship between S4/S1 and S3/S2 and the brands of recording paper, according to the second example embodiment of the present invention.

In the third modification of the second example embodiment illustrated in FIG. 34, the values of S4/S1, S3/S2, and St are measured for every brand of recording paper compatible with the color printer 2000 and the results are stored in the ROM 112 of the processing device 110 as a recording paper identification table, in advance of shipment, for example, when adjustment processes are performed in the factory FIG. 35 illustrates the relationship between S4/S1 and S3/S2 and the brands of recording paper, according to the second example embodiment of the present invention.

As described above, a plurality of photosensors are provided to detect the light diffused to several different directions, and the type of recording paper is determined based on the calculated values such as the ratio of the output values of the photosensors. Accordingly, precise determination becomes possible in spite of the existing disturbance light or stray light.

In the present modification, the printer controller 2090 may select several candidate brands of recording paper from the measurement values of S1 and S2, and these candidate brands can be narrowed down to a single brand in consideration of the values of S4/S1, S3/S2, and St.

In the third modification of the second example embodiment, S4/S1 is used for determination when the values of S1 and S4 are obtained. However, no limitation is indicated therein. In a similar manner, no limitation is indicated to the use of S3/S2 when the values of S2 and S3 are obtained.

Figure 36A:
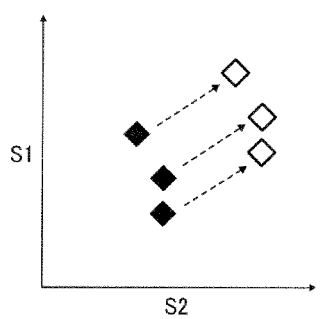
FIGS. 36A and 36B illustrate the influence of disturbance light according to the second example embodiment of the present invention.
Figure 36B:
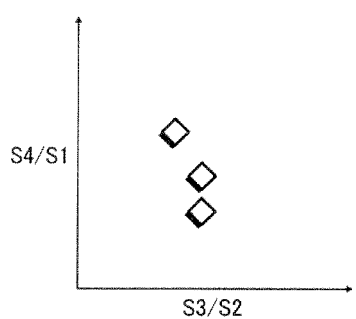

FIGS. 36A and 36B illustrate the influence of disturbance light according to the second example embodiment of the present invention. More specifically, a case in which determination is made with S1 and S2 only is compared with a case in which determination is made with S4/S1 and S3/S2, in regard to the influence of disturbance light. As illustrated in FIG. 36A, when disturbance light is present and determination is made with S1 and S2 only, the values detected by photosensors increase, which may lead to erroneous determination. By contrast, as illustrated in FIG. 36B, when disturbance light is present and determination is made with S4/S1 and S3/S2, the values detected by photosensors are substantially unchanged. This leads to accurate determination.

In addition to the photosensor 17, the photosensor 19, and the polarizing filter 18 as described above, a photosensor that detects the amount of the surface diffuse reflection light in a similar manner to the photosensor 17 (this photosensor is referred to as a photosensor 22), a polarizing filter that is similar to the polarizing filter 18 (this photosensor is referred to as a polarizing filter 24), and a photosensor that receives the light that has passed the polarizing filter 24 (this photosensor is referred to as a photosensor 23) may further be provided. Here, the output levels of the photosensor 22 and the photosensor 23 are referred to as "S5" and "S6", respectively. In this case, paper-type discrimination may be performed by using the values of (S4/S1+S6/S1), (S3/S2+S5/S2), and St. Moreover, paper-type discrimination may be performed by using the values of S4/S1, S6/S1, S3/S2, S5/S2, and St. As a matter of course, a recording paper identification table is generated for the calculation of paper-type discrimination in advance of shipment, for example, when adjustment processes are performed in the factory, and is stored in the ROM of the printer controller 2090.

In the second example embodiment described above, an optical displacement sensor that irradiates recording paper with light and receives the light reflected from the recording paper by using a position sensitive detector (PSD) or image sensor may be provided in place of the displacement sensor 54.

In the second example embodiment described above, the processing device 110 may notify the printer controller 2090 of the obtained values of S1, S2, and St, and the printer controller 2090 may determine the brand of recording paper. In this case, a recording paper identification table is stored in the ROM of the printer controller 2090.

In the second example embodiment described above, a power source may be integrated into the sensor apparatus 100. In that case, the power supply from the color printer 2000 is not necessary.

In the second example embodiment described above, data may be communicated by radio between sensor apparatus 100 and the printer controller 2090.

In the second example embodiment described above, the sensor apparatus 100 may be provided with an LED that illuminates when recording paper is detected by the paper sensor 53. Due to such provision of an LED, an operator can easily notice that recording paper has been inserted to a specified position.

In the second example embodiment described above, sensor apparatus 100 may obtain the signals output from photosensors for every specified sampling period. For example, when p pieces of data are obtained from each photosensor, the output levels of the p pieces of data are averaged, and the obtained average value may be used as a measurement value.

In the second example embodiment described above, the processing device 110 may be removed from the sensor apparatus 100, and an independent processing device may be provided outside the sensor apparatus 100 to identify recording paper based on the signals output from photosensors and the signal output from the displacement sensor 54.

In the second example embodiment described above, the sensor apparatus 100 is described as a stationary apparatus. However, no limitation is indicated therein, and a sensor apparatus 200 that is portable may be provided instead.

The sensor apparatus 200 may be detached from the printer cabinet 2200, and is arranged near the operation panel such that an operator can pick it up with his/her hand.

Figure 37:
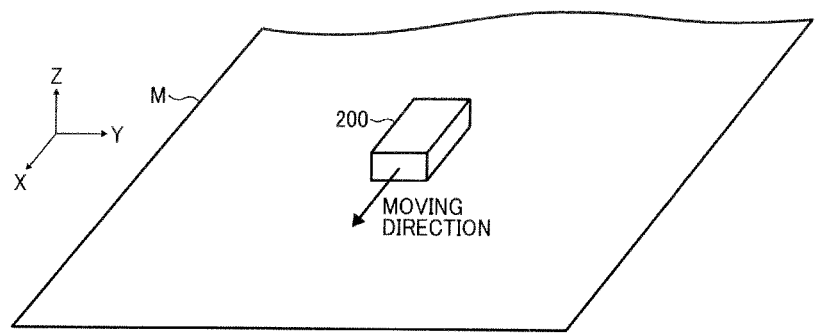
FIG. 37 illustrates a second sensor apparatus that is portable, according to the second example embodiment of the present invention.
Figure 38:
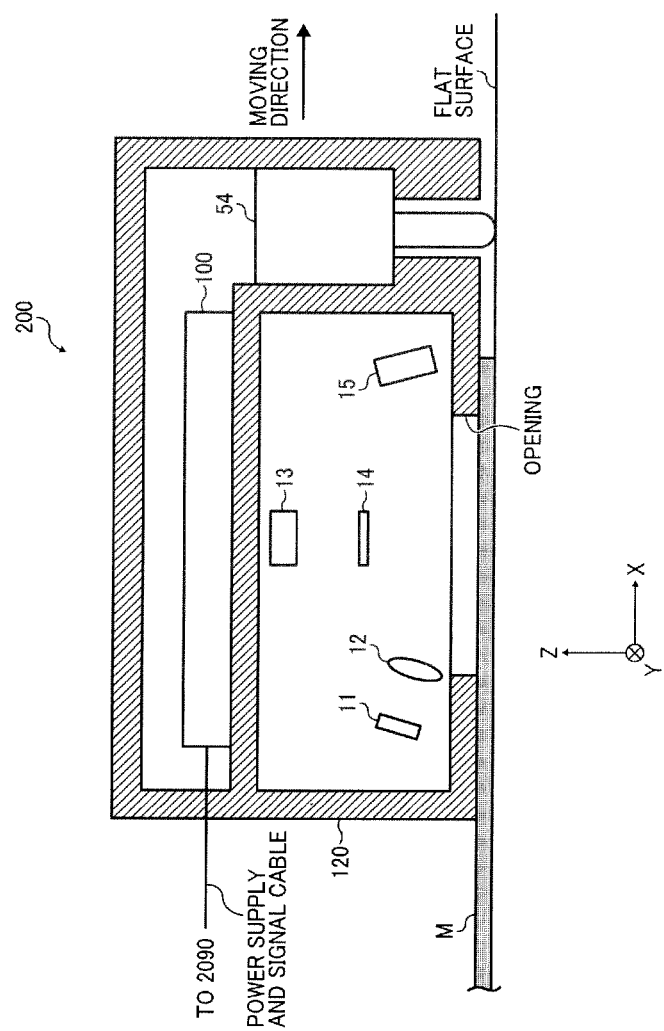
FIG. 38 illustrates the configuration of a second sensor apparatus according to the second example embodiment of the present invention.

FIG. 37 illustrates a portable version of the sensor apparatus 200, according to the second example embodiment of the present invention. As illustrated in FIG. 37, when the brand of recording paper is to be determined, the sensor apparatus 200 is moved on the surface of the recording paper M. FIG. 38 illustrates the XZ cross section of the sensor apparatus 200 according to the second example embodiment of the present invention. In the configuration described in FIG. 38, the optical sensor and the displacement sensor 54 are close to each other in the direction parallel with the surface of the recording paper M (i.e., X-axis direction). Here, the +X direction is the moving direction of the sensor apparatus 200, and the displacement sensor 54 is arranged on the +X side of the optical sensor.

The brand determination processes with the use of the sensor apparatus 200 according to the present example embodiment are described.

Firstly, the operation performed by an operator in the brand determination processes are described.

Figure 39A:
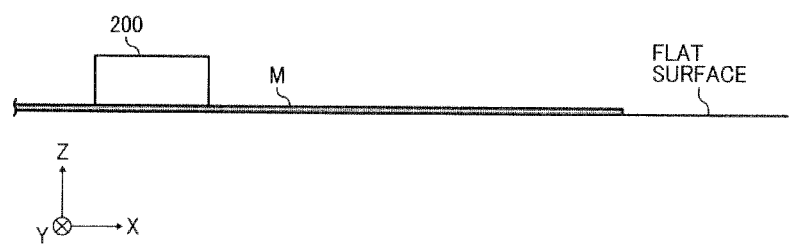
FIGS. 39A to 39C illustrate a brand-determination process for recording paper performed by a second sensor apparatus, according to the second example embodiment of the present invention.
Figure 39B:
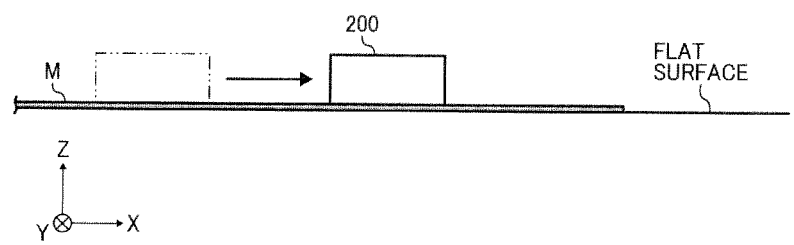
Figure 39C:
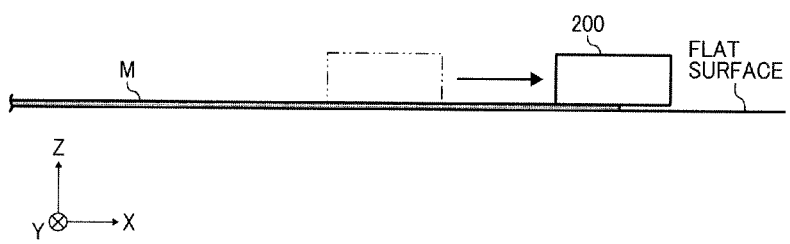

1. The recording paper M is placed on the flat surface arranged near the operation panel.
2. The sensor apparatus 200 is grabbed, and the sensor apparatus 200 is placed on the recording paper M (see FIG. 39A).
3. A request for a determination process is made through the operation panel. This request for a determination process is sent to the processing device 110 of the sensor apparatus 200 through the operation panel and the printer controller 2090.
4. The sensor apparatus 200 is moved towards the +X direction (see FIG. 39B).
5. When at least a part of the displacement sensor 54 of the sensor apparatus 200 is off the recording paper M and is placed above the flat surface (see FIG. 39C), the movement of the sensor apparatus is stopped.

Once the request for a determination process is received, the processing device 110 starts a brand determination process.

(1) A plurality of light-emitting units of the light source 11 are switched on at the same time.
(2) The values of S1 and S2 are calculated from the signals output from the photosensors.
(3) When the displacement sensor 54 of the sensor apparatus 200 is off the recording paper M and is placed above the flat surface, the number of pulses St output from the displacement sensor 54 is measured.
(4) The light-emitting units of the light source 11 are switched off.
(5) The recording paper identification table is referred to, and the brand of the recording paper is determined based on the obtained values of S1, S2, and St.
(6) The printer controller 2090 is notified of the result of the determination. Then, the brand determination process is terminated.

A mark (for example, an arrow) may be drawn on the sensor cabinet 120 of the sensor apparatus 200 to indicate the moving direction of the sensor apparatus 200.

In the sensor apparatus 200, the displacement sensor 54 may additionally be provided on the −X side of the optical sensor. In that case, the sensor apparatus 200 may be moved in both the +X direction and −X direction.

Additionally the sensor apparatus 100 may be divided into an optical sensor 2245 and a thickness sensor 2246, as described below.

Figure 40:
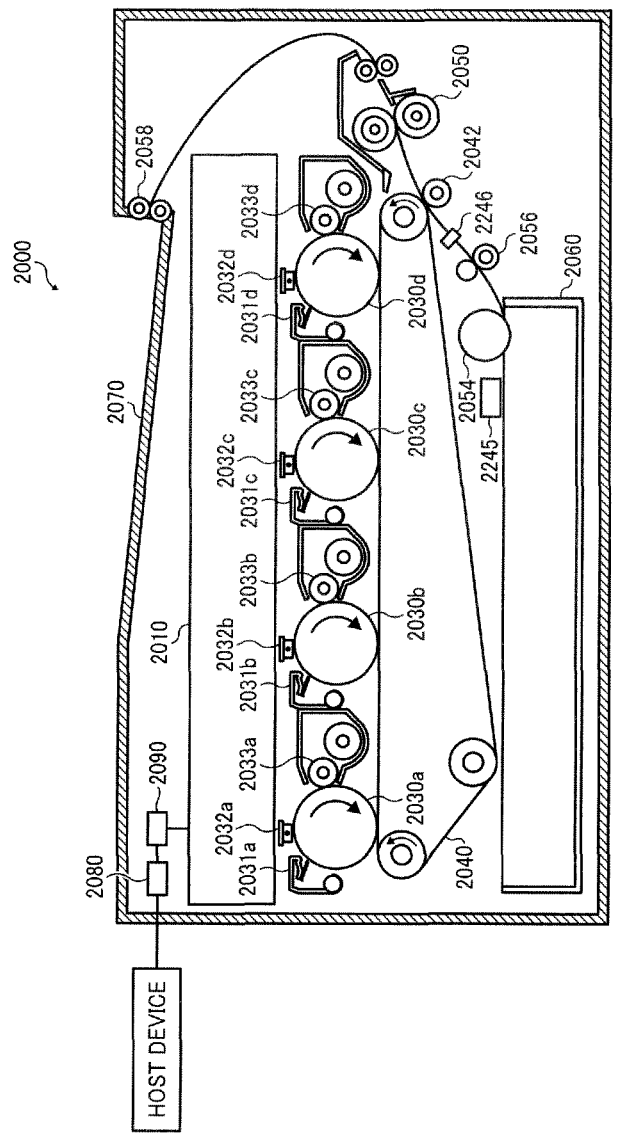
FIG. 40 illustrates an example of arrangement in which a sensor apparatus is divided into an optical sensor and a thickness sensor, according to the second example embodiment of the present invention.

FIG. 40 illustrates an example of arrangement in which the sensor apparatus 100 is divided into the optical sensor 2245 and the thickness sensor 2246, according to the second example embodiment of the present invention. In FIG. 40, the optical sensor 2245 is arranged near the paper feed tray 2060, and the thickness sensor 2246 is arranged in the conveyance path of recording paper taken from the paper feed tray 2060.

Figure 41:
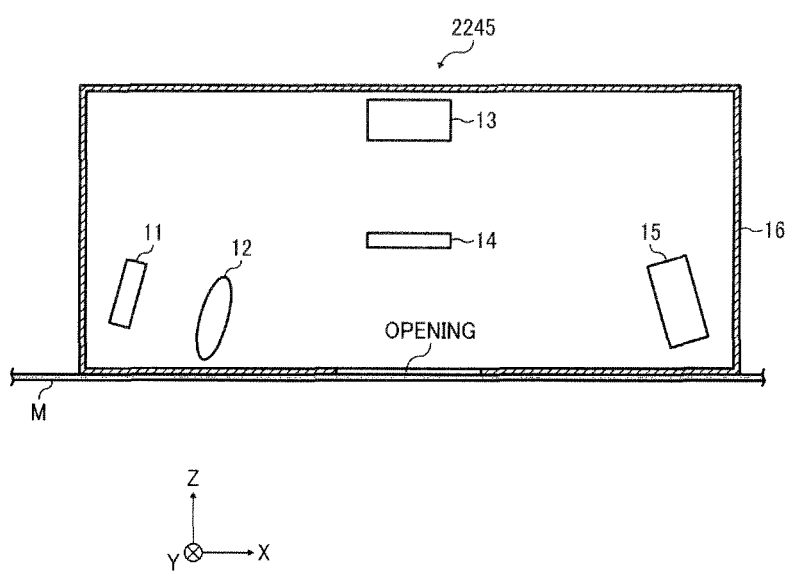
FIG. 41 illustrates the configuration of an optical sensor according to the second example embodiment of the present invention.

FIG. 41 illustrates an example of the configuration of the optical sensor 2245 according to the second example embodiment of the present invention. As illustrated in FIG. 41, the optical sensor 2245 includes the light source 11, the collimate lens 12, the photosensors 13 and 15, the polarizing filter 14, and the dark box 16 that encloses these elements.

The dark box 16 according to the second example embodiment is a box whose inner surface is treated to reduce the influence of disturbance light and stray light, for example, by choosing a specific color for the material, painting the surface, chemically staining the surface, and processing the surface with scratch-brush finish.

FIG. 42 illustrates an example of the configuration of the thickness sensor 2246 according to the second example embodiment. As illustrated in FIG. 42, the thickness sensor 2246 includes a paper feeding guide 51, guide rollers 52a, 52b, and 52c, paper sensors 53a and 53b, the displacement sensor 54, and a metallic or engineering-plastic holding member that holds these elements. In the thickness sensor 2246 of FIG. 42, it is assumed that the direction orthogonal to the surface of the recording paper M is the z-axis direction, and the x-axis direction and y-axis direction are orthogonal to each other and are on the surface that is orthogonal to the z-axis direction. Moreover, it is assumed in the thickness sensor 2246 that the direction of travel of the recording paper M is the +x direction.

The paper feeding guide 51 is made of metal or engineering plastic. The +z side surface of the paper feeding guide 51 is the surface on which the recording paper M is conveyed, and serves as a reference plane when the thickness of the recording paper M is measured.

The guide rollers 52a, 52b, and 52c are arranged on the +z side of the paper feeding guide 51, and press the recording paper M against the +z side surface of the paper feeding guide 51 to prevent the recording paper M from floating up from the reference plane. Each of the guide rollers 52a, 52b, and 52c is made, for example, by placing rubber over the surface of a metallic shaft.

The paper sensors 53a and 53b are arranged on the +z side of the paper feeding guide 51 to detect the presence of the recording paper M. For example, the paper sensors 53a and 53*b* transmit binary signals. More specifically, each of the paper sensors 53*a* and 53*b* transmits a high-level (H) signal to the printer controller 2090 when the recording paper M is detected, and each of the paper sensors 53*a* and 53*b* transmits a low-level (L) signal to the printer controller 2090 when the recording paper M is not detected. A signal output from each of the paper sensors 53*a* and 53*b* serves as a timing signal used by the printer controller 2090 to measure the thickness of the recording paper M.

The displacement sensor 54 is, for example, a cantilever displacement sensor, and is placed on the +z side of the paper feeding guide 51. For example, the displacement sensor 54 converts into the number of pulses the amount of the displacement caused to the cantilever in the +z direction with reference to the reference plane, and transmits the obtained number of pulses to the printer controller 2090.

Next, the operation of the thickness sensor 2246 is described.

Figure 43A:
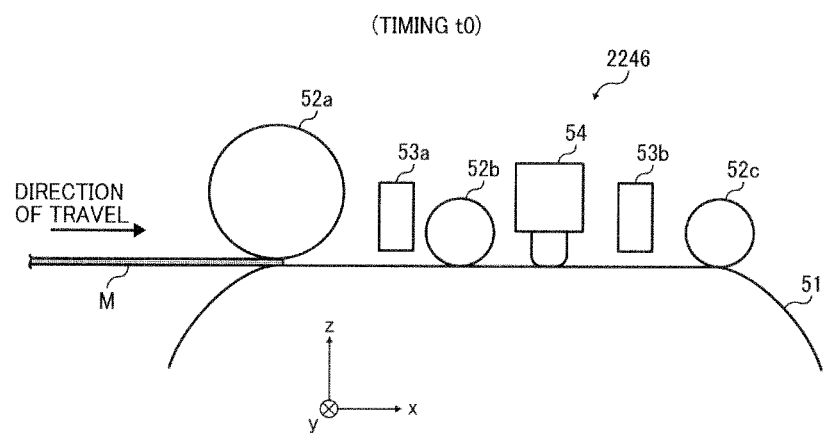
FIG. 43A illustrates timing t0 of a thickness sensor according to the second example embodiment of the present invention.

(1) When the front end of the recording paper M is inserted between the guide roller 52*a* and the paper feeding guide 51 at timing t0, the recording paper M is pressed against the reference plane by the guide roller 52*a* (see FIG. 43A).

Figure 43B:
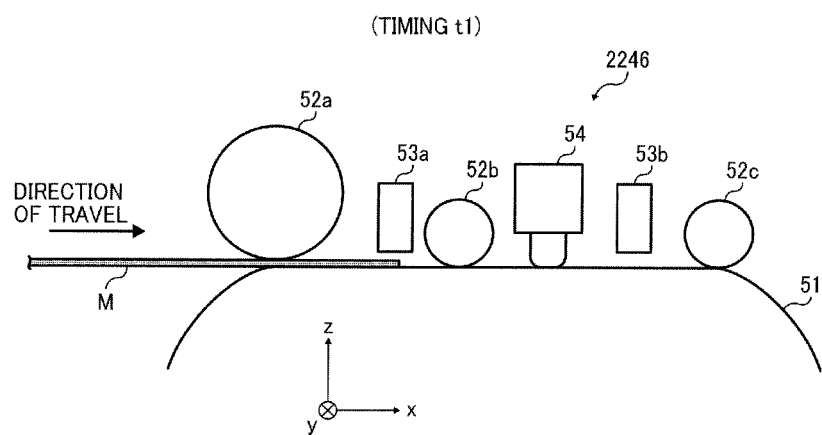
FIG. 43B illustrates timing t1 of a thickness sensor according to the second example embodiment of the present invention.

(2) When the recording paper M moves towards the +x direction and the front end of the recording paper M reaches the detection area of the paper sensor 53*a* at timing t1 (see FIG. 43B), the level of the signal output from the paper sensor 53*a* changes from the L-level to the H-level.

(3) When the recording paper M further moves towards the +x direction and the front end of the recording paper M is inserted between the guide roller 52*b* and the paper feeding guide 51, the recording paper M is pressed against the reference plane by the guide roller 52*b*.

Figure 44A:
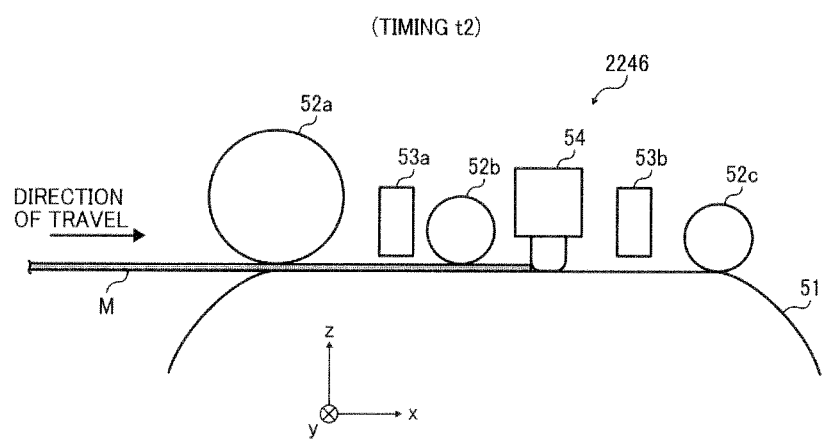
FIG. 44A illustrates timing t2 of a thickness sensor according to the second example embodiment of the present invention.

(4) When the recording paper M further moves towards the +x direction and the front end of the recording paper M touches the cantilever of the displacement sensor 54 at timing t2 (see FIG. 44A), the cantilever starts to be displaced in the +z direction.

(5) When the recording paper M further moves towards the +x direction, the cantilever is displaced in the +z direction with reference to the reference plane by the thickness of the recording paper M. Then, the displacement sensor 54 transmits the pulses whose number corresponds to the level of the displacement caused to the cantilever of the displacement sensor 54.

Figure 44B:
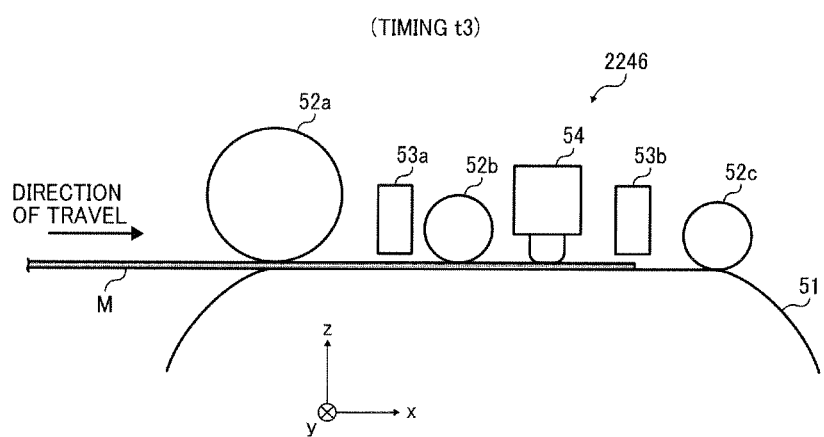
FIG. 44B illustrates timing t3 of a thickness sensor according to the second example embodiment of the present invention.

(6) When the recording paper M further moves towards the +x direction and the front end of the recording paper M reaches the detection area of the paper sensor 53*b* at timing t3 (see FIG. 44B), the level of the signal output from the paper sensor 53*b* changes from the L-level to the H-level.

(7) When the recording paper M further moves towards the +x direction and the rear end of the recording paper M passes the detection area of the paper sensor 53*a*, the level of the signal output from the paper sensor 53*a* changes from the H-level to the L-level.

(8) When the recording paper M further moves towards the +x direction and the rear end of the recording paper M passes the detection area of the paper sensor 53*b*, the level of the signal output from the paper sensor 53*b* changes from the H-level to the L-level.

The printer controller 2090 measures the number of the pulses output from the displacement sensor 54 since the level of the signal output from the paper sensor 53*a* changes from the L-level to the H-level and until the level of the signal output from the paper sensor 53*b* changes from the L-level to the H-level (see FIG. 45).

Next, processes in which the brand of recording paper stored in the paper feed tray 2060 is determined (brand determination processes) are described. The brand determination processes are performed by the printer controller 2090.

(1) A plurality of light-emitting units of the light source 11 are switched on at the same time.

(2) The values of S1 and S2 are obtained from the photosensors 13 and 15, respectively.

(3) The recording paper is conveyed from the paper feed tray 2060, and the number of the pulses St output from the displacement sensor 54 is measured.

(4) The light-emitting units of the light source 11 are switched off.

(5) The recording paper identification table is referred to, and the brand of the recording paper is determined based on the obtained values of S1, S2, and St.

(6) The identified brand of the recording paper is stored in the RAM, and the paper-type discrimination process is terminated.

Figure 46:
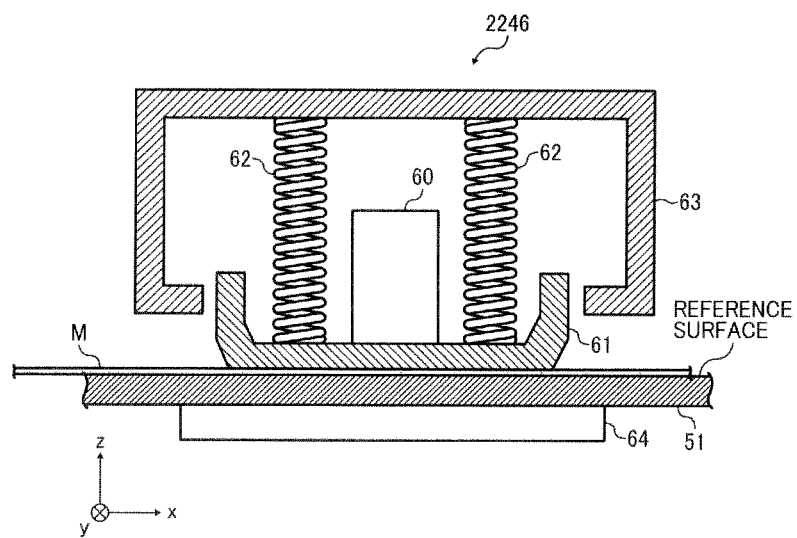
FIG. 46 illustrates a first modification of a thickness sensor according to the second example embodiment of the present invention.

FIG. 46 illustrates a first modification of the thickness sensor 2246 according to the second example embodiment of the present invention. In place of the displacement sensor 54, an eddy current type or capacitance-type displacement sensor 60 may be provided. In this case, the displacement sensor 60 is mounted on the pressing member 61 that presses the recording paper M against the paper feeding guide 51, such that the sensing surface of the displacement sensor 60 faces the pressing member 61. The pressing member 61 is attached to the holding member 63 through the spring members 62. The holding member 63 is fixed to a member made of metal or engineering plastic.

When the recording paper M is not present, the pressing member 61 is in contact with the +z side surface of the paper feeding guide 51 as pressed by the spring members 62. While the recording paper M is passing through the space between the paper feeding guide 51 and the pressing member 61, the displacement sensor 60 outputs the amount of change in the distance (space) between the pressing member 61 and the paper feeding guide 51. Note that in order for an eddy current type or capacitance-type displacement sensor to function property, at least some portion of the reference plane that faces the displacement sensor needs to be metallic. For this reason, at least the surface of the paper feeding guide 51 that faces the pressing member 61 needs to be metal, or a metallic plate 64 needs to be attached underneath the surface of the paper feeding guide 51 that faces the pressing member 61. Moreover, the pressing member 61 needs to be nonmetal.

Figure 47:
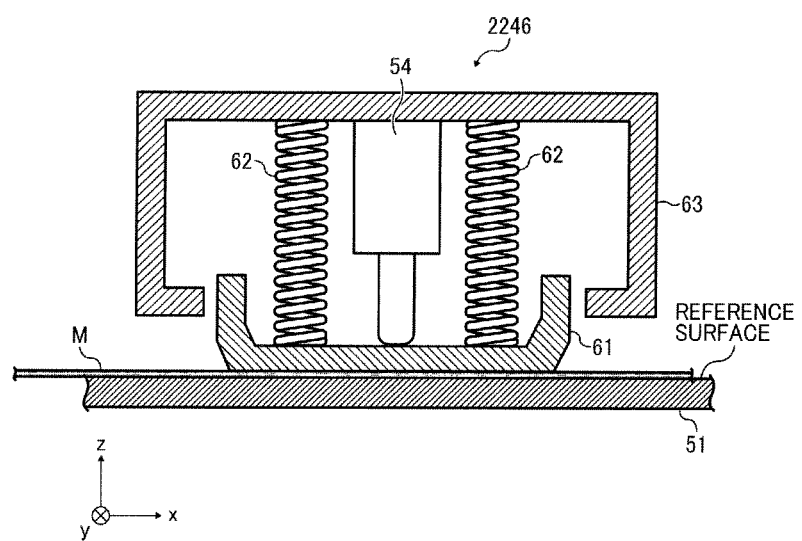
FIG. 47 illustrates a second modification of a thickness sensor according to the second example embodiment of the present invention.

FIG. 47 illustrates a second modification of the thickness sensor 2246 according to the second example embodiment. As illustrated in FIG. 47, the displacement sensor 54 may be arranged such that its cantilever is in contact with the +z side surface of the pressing member 61. Also in this case, while the recording paper M is passing through the space between the paper feeding guide 51 and the pressing member 61, the pulses whose number is proportionate to the thickness of the recording paper are output. In the second modification of the second example embodiment, the pressing member 61 may be made of metal, which is different from the first modification of the second example embodiment in which the eddy current type or capacitance-type displacement sensor 60 is used. Moreover, even when the paper feeding guide 51 is nonmetal, the metallic plate 64 illustrated in FIG. 46 is not necessary.

Note that the position at which the optical sensor 2245 is arranged is not limited to the proximity of the paper feed tray 2060. Moreover, the thickness sensor 2246 is not necessarily arranged on the conveyance path of the recording paper taken from the paper feed tray 2060. The optical sensor 2245 and the thickness sensor 2246 may be arranged so as to be close to each other.

Figure 48:
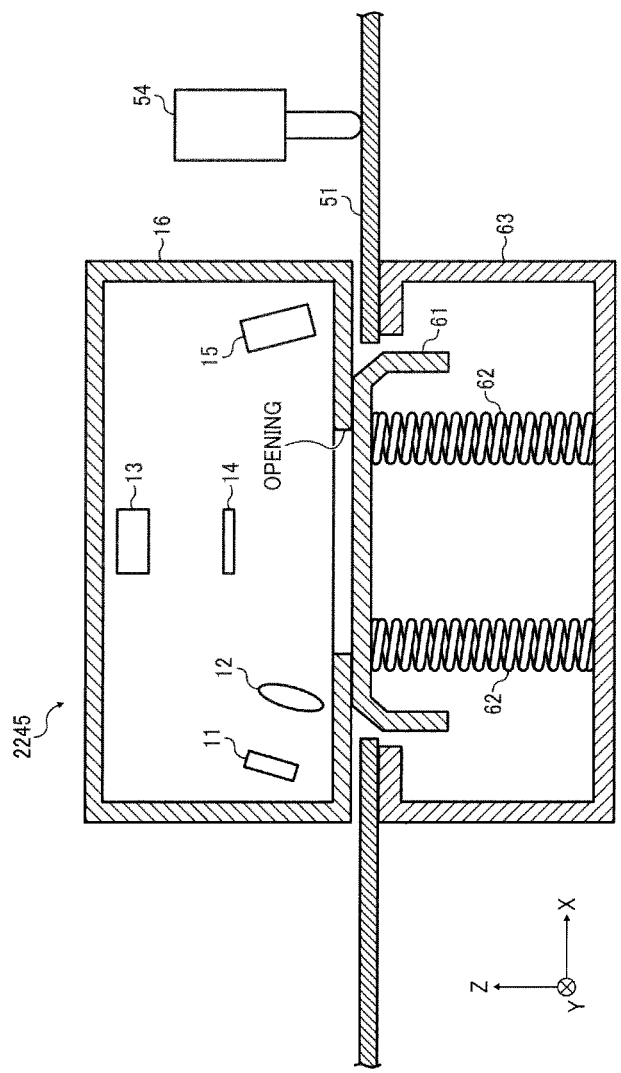
FIG. 48 illustrates Example 1 of arrangement in which an optical sensor and a displacement sensor are close to each other, according to the second example embodiment of the present invention.
Figure 49:
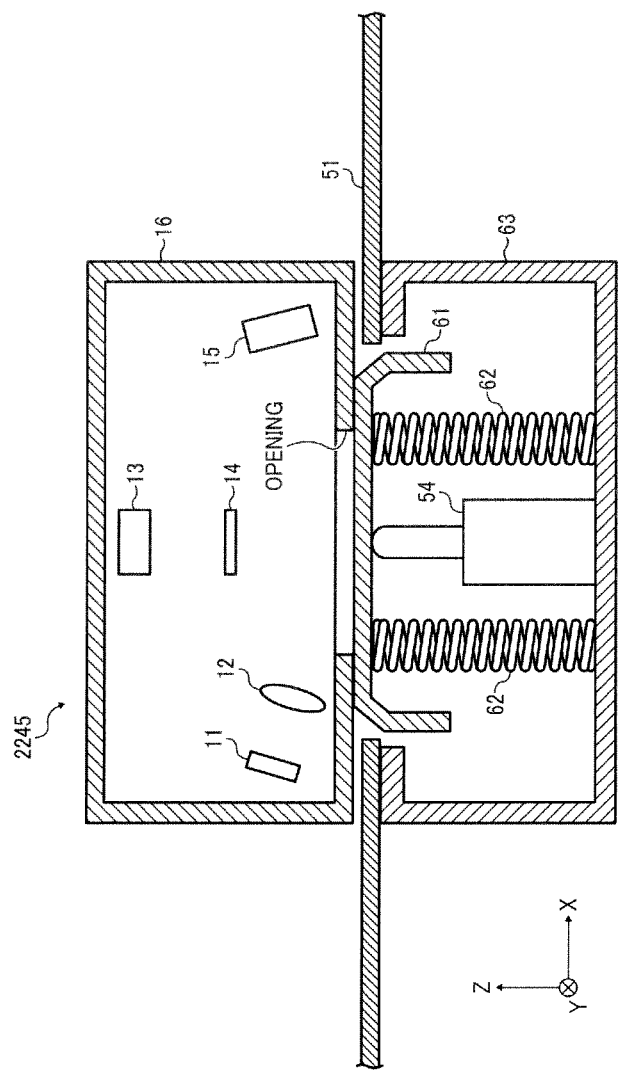
FIG. 49 illustrates Example 2 of arrangement in which an optical sensor and a displacement sensor are close to each other, according to the second example embodiment of the present invention.

FIG. 48 illustrates Example 1 of arrangement in which the displacement sensor 54 is arranged near the optical sensor 2245, according to the second example embodiment. FIG. 49 illustrates Example 2 of arrangement in which the displacement sensor 2245 is arranged so as to face the optical sensor 2245 across the recording paper M, according to the second example embodiment.

The sensor apparatus 100 may be applied to an image forming apparatus in which an image is formed by ejecting ink onto recording paper.

Third Embodiment

Next, the third example embodiment of the present invention is described with reference to FIG. 50. The color printer 2000 according to the third example embodiment uses a sensor apparatus 300 in place of the sensor apparatus 100. In regard to the other aspects of the configuration, the color printer 2000 according to the third example embodiment is equivalent to that of the second example embodiment described above. For this reason, the description concentrates on the differences from the second example. In the description of the third example embodiment, like reference signs are given to elements similar to those described in the second example embodiment, and the description of such similar elements are omitted.

Figure 50:
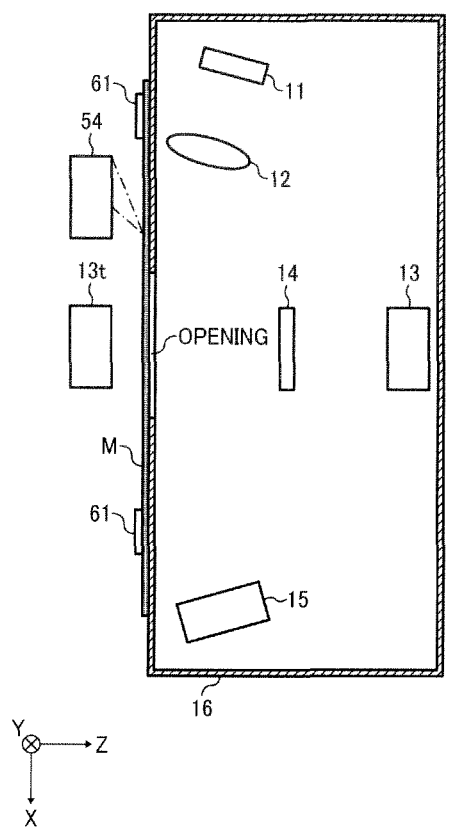
FIG. 50 illustrates the configuration of a sensor apparatus according to the third example embodiment of the present invention.

As illustrated in FIG. 50 as an example, the sensor apparatus 300 includes the light source 11, the collimate lens 12, the photosensors 13, 13t, and 15, the polarizing filter 14, the displacement sensor 54, the pressing member 61, the dark box 16, and the processing device 110. Note that the light source 11, the collimate lens 12, the photosensors 13, 13t, and 15, the polarizing filter 14 of the sensor apparatus 300 form an optical sensor.

In order to prevent paper dust from entering the sensor apparatus 100, the opening of the dark box 16 is sealed by a transparent member.

Because the light that passes through the recording paper is dispersed by the fibers of the recording paper, the amount of the transmission light decreases when the recording paper is thick, i.e., when the basis weight is greater. The regression curve that indicates the relationship between the basis weight and transmission light quantity of recording paper is referred to as a basis weight estimation curve. The basis weight estimation curve varies depending on the type of paper, and thus the basis weight estimation curve is obtained in advance for each type of recording paper.

Next, processes in which the brand of the recording paper M is determined (brand determination processes) are described.

Firstly, the operation performed by an operator in the brand determination processes are described.

1. The recording paper M is inserted between the pressing member 61 and the dark box 16.

2. A request for a determination process is made through an operation panel. This request for a determination process is sent to the processing device 110 of the sensor apparatus 300 through the operation panel and the printer controller 2090.

3. After a specified period of time (for example, five seconds), the recording paper M is pulled out from between the pressing member 61 and the dark box 16.

Once the request for a determination process is received, the processing device 110 starts a brand determination process.

(1) The signal output from the displacement sensor 54 is referred to, and when it is confirmed that the recording paper M is at a specified position, a plurality of light-emitting units of the light source 11 are switched on at the same time.

(2) The values of S1, S2, and ST are calculated from the signals output from the photosensors.

(3) The number of the pulses St output from the displacement sensor 54 is measured when the recording paper M is pulled out.

(4) The light-emitting units of the light source 11 are switched off.

(5) The recording paper identification table is referred to, and the brand of the recording paper is determined based on the obtained values of S1, S2, and at least one of ST and St. When several candidate brands are determined in this step, such candidate brands can be narrowed down to a single brand as follows.

(6) The type of the recording paper is determined based on the obtained value of S2. In this step, it is determined that the recording paper is, for example, plain paper or gloss coated paper.

(7) The thickness of the recording paper is estimated from the obtained values of S2 and St.

(8) Whether the estimated thickness is equal to or greater than a specified value is determined, and when the estimated thickness is equal to or greater than the specified value, the basis weight of the recording paper is estimated from the obtained values of S2 and St. On the other hand, when the estimated thickness is less than the specified value, the basis weight of the recording paper is estimated from the obtained values of S2, St, and ST.

(9) The brand of the recording paper is determined based on the results obtained in step (5) and steps (6) to (8). Note that the brand determination process described above is merely an example, and no limitation in limited therein.

(10) The printer controller 2090 is notified of the result of the determination. Then, the brand determination process is terminated.

The printer controller 2090 controls the display of the operation panel to display the determination results obtained from the processing device 110, and stores these determination results in the RAM of the printer controller 2090.

When the identified brand of the recording paper is displayed on the display of the operation panel, an operator sets the recording paper of the specified brand to the paper feed tray 2060. The brand of the recording paper displayed on the display of the operation panel may be registered into the printer controller 2090 by using the keys on the operation panel.

Then, the printer controller 2090 reads the brand of the recording paper from the RAM when a request for a print job is received, and then determines optimal developing conditions and transferring conditions from the development and transfer table for the specified brand of the recording paper.

Then, the printer controller 2090 controls the development device and transfer device of each image forming station in accordance with the determined optimal developing conditions and transferring conditions. For example, the printer controller 2090 controls the transfer voltage or the amount of toner. Accordingly, a high-quality image is formed on recording paper.

Conventionally, the glossiness of the surface of recording paper is detected from the light quantity of the regular reflection, and the smoothness of the surface of the recording paper is detected from the ratio of the light quantity of the regular reflection to the light quantity of the diffuse reflection, in order to determine the type of the recording paper. By contrast, in the third example embodiment, an optical sensor and a displacement sensor are used to detect the transmission light and the diffuse reflection light from the inside of the recording paper to obtain information including other properties of the recording paper such as the thickness and density of the recording paper. Further, the output from the displacement sensor is detected. Accordingly, identification accuracy is improved.

For example, it was difficult to distinguish plain paper from matte coated paper with only the information of the surface of recording paper, which is used in the conventional identification technique. In the third example embodiment, the information of the inside of recording paper is also used in addition to the information of the surface of recording paper. Accordingly, it becomes possible to distinguish a number of brands of plain paper and a number of brands of matte coated paper in addition to the distinction between plain paper and matte coated paper. Further, the thickness information of the recording paper is added, and it becomes possible to more precisely distinguish a number of brands of plain paper and a number of brands of matte coated paper. In other words, according to the present example embodiment, it becomes possible to determine the brand of an object by detecting a difference in thickness and at least one of glossiness, smoothness, and density of the recording paper.

Alternatively, the brand of the recording paper may be determined as follows. Several candidate brands are determined based on the measurement values of Sa and S2, and these candidate brands are narrowed down to a single brand in consideration of the measurement value of St.

Further, the brand of the recording paper may be determined as follows. Several candidate brands are determined based on the measurement value of St, and these candidate brands are narrowed down to a single brand in consideration of the measurement values of S1 and S2.

Alternatively, the brand of the recording paper may be determined as follows. Several candidate brands are determined based on the measurement values of S1 and S2, and these candidate brands are narrowed down to a single brand in consideration of the measurement value of ST.

Alternatively, the brand of the recording paper may be determined as follows. Several candidate brands are determined based on the measurement value of ST, and these candidate brands are narrowed down to a single brand in consideration of the measurement values of S1 and S2.

The priority among the displacement sensor 54, the photosensor 13t, and the photosensor 13 in regard to the information about the thickness of recording paper is as follows: displacement sensor 54>photosensor 13t>photosensor 13. Here, the design concept of the third example embodiment is described.

The displacement sensor 54 has high basis weight estimation accuracy for thick paper, but has low basis weight estimation accuracy for thin paper. This is because an error in the measurement of the displacement sensor 54 is made for only mechanical reason, and is not dependent on the thickness of paper. Accordingly, a relative error is smaller for thick paper.

The photosensor 13t has high basis weight estimation accuracy for thin paper, but has low basis weight estimation accuracy for thick paper. This is because thin paper easily transmits light and the correlation between transmission light quantity and basis weight is high, and thick paper transmits only a small amount of light and the S/N is small. Moreover, thick paper may be a board (with layered structure, some of which has white surface but has an inner layer that absorbs a large amount of light), or the surface of thick paper may be uneven. In such cases, the correlation between transmission light quantity and basis weight becomes low.

The output from the photosensor 13 indicates the fiber structure or density, material, or thickness of recording paper. However, the light received by the photosensor 13 includes polarized components of the mutiplex diffuse reflection light from the surface. For this reason, the measurement values obtained by the photosensor 13 are based on the paper thickness and basis weight, but are not precise enough to perform direct estimation.

In the third example embodiment, basis weight is estimated by performing weighted calculation. More specifically, the output from the displacement sensor 54 is used for calculating the basis weight of thick paper, and the output from both the photosensor 13t and the photosensor 13 is used for calculating the basis weight of thin paper.

As described above, the sensor apparatus 300 according to the present example embodiment includes, for example, the light source 11, the collimate lens 12, the photosensors 13, 13t, and 15, the polarizing filter 14, the displacement sensor 54, the pressing member 61, and the processing device 110. Note that the light source 11, the collimate lens 12, the photosensors 13, 13t, and 15, the polarizing filter 14 of the sensor apparatus 300 form an optical sensor.

The light source 11 and the collimate lens 12 form an irradiation system, and the irradiation system emits the s-polarized light to recording paper in a direction oblique to the z-axis direction. The photosensor 15 is arranged on the optical path of the light that is emitted from the irradiation system and then is reflected at the recording paper by regular reflection (surface regular reflection light). The polarizing filter 14 and the photosensor 13 are arranged on the optical path of the light that is reflected by diffuse reflection in the direction of the normal line drawn from the surface of the recording paper. The polarizing filter 14 transmits the p-polarized light, and the photosensor 13 receives the light that has passed through the polarizing filter 14 (i.e., the p-polarized light included in the internal reflection light). The photosensor 13t receives the light that has passed through the recording paper. The displacement sensor 54 detects the thickness of the recording paper.

The processing device 110 determines the brand of recording paper based on the signals output from the photosensors and the signal output from the displacement sensor 54.

As described above, the light quantity of the p-polarized light included in the internal reflection light is detected. Accordingly, it becomes possible to achieve precise separation of the internal reflection light. Conventionally, such separation of the light reflected from the inside of recording paper was difficult to achieve. The reflection light from the inside of recording paper includes the information about the inside state of the recording paper. Thus, by detecting the amount of the transmission light that includes the thickness information of an object, it becomes possible to improve the level of paper discrimination such that the level of the recording paper can be determined. Conventionally, such determination of brand was difficult. The thickness of recording paper is detected in the present example embodiment, and this also contributes to the improvement of discrimination accuracy.

Accordingly, the processing device 110 can identify the type of recording paper more precisely than the conventional technique.

Because the light source 11 includes a plurality of light-emitting units, the light quantity of the p-polarized light included in the internal reflection light or the transmission light quantity can be increased by switching on all the light-emitting units at the same time.

Due to the provision of the sensor apparatus 300, the color printer 2000 according to the third example embodiment can form a high-quality image. Further, troublesome manual settings or failure in printing due to a setting error, which are still present in the conventional products, can be eliminated in the present example embodiment.

The number of the photosensors may be increased when an error is expected due to disturbance light or stray light.

Figure 51:
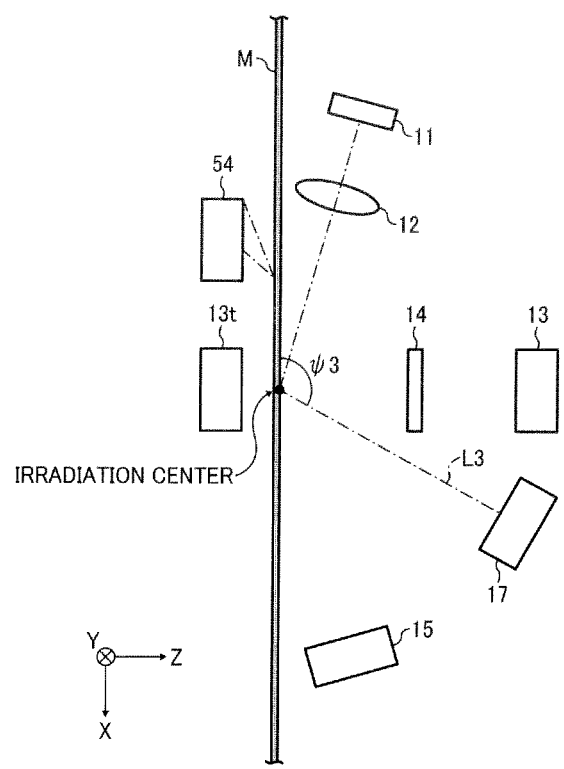
FIG. 51 illustrates a first modification of an optical sensor, according to the third example embodiment of the present invention.

FIG. 51 illustrates a first modification of an optical sensor, according to the third example embodiment. As illustrated in FIG. 51, for example, the optical sensor 2245 may further include the photosensor 17. As illustrated in FIG. 51, reflection light including the surface diffuse reflection light and internal reflection light enters the photosensor 17. At this light receiving position, the amount of the internal reflection light is very small compared with the amount of the surface diffuse reflection light. For this reason, it can be assumed that the amount of the light received at the photosensor 17 is substantially equivalent to the amount of the surface diffuse reflection light.

As illustrated in FIG. 51, for example, the angle ψ3 between the surface of the recording paper M and a line L3, which is drawn from the irradiation center to the center of the photosensor 17, is 120 degrees. Note that the center of the light source 11, the irradiation center, the center of the polarizing filter 14, and the centers of the photosensors are substantially on the same plane.

The brand determination processes performed by the processing device 110 in the case of the third modification according to the third example embodiment are described as follows. Assuming that the recording paper M is irradiated with the light flux emitted from the light source 11, the signal level of the signal output from the photosensor 17 is referred to as "S4".

(1) The signal output from the displacement sensor 54 is referred to, and when it is confirmed that the recording paper M is at a specified position, a plurality of light-emitting units of the light source 11 are switched on at the same time.

(2) The values of S1, S2, S4, and ST are calculated from the signals output from the photosensors.

(3) The number of the pulses St output from the displacement sensor 54 is measured when the recording paper M is pulled out.

(4) The light-emitting units of the light source 11 are switched off.

(5) The value of S4/S2 is calculated.

(6) The recording paper identification table is referred to, and the brand of the recording paper is determined based on the obtained values of S1, S4/S2, St, and at least one of ST and St.

(7) The printer controller 2090 is notified of the result of the determination. Then, the brand determination process is terminated.

In the first modification of the third example embodiment illustrated in FIG. 51, the values of S1, S4/S2, St, and ST are measured for every brand of recording paper compatible with the color printer 2000 and the results are stored in the processing device 110 as a recording paper identification table, in advance of shipment, for example, when adjustment processes are performed in the factory.

Figure 52:
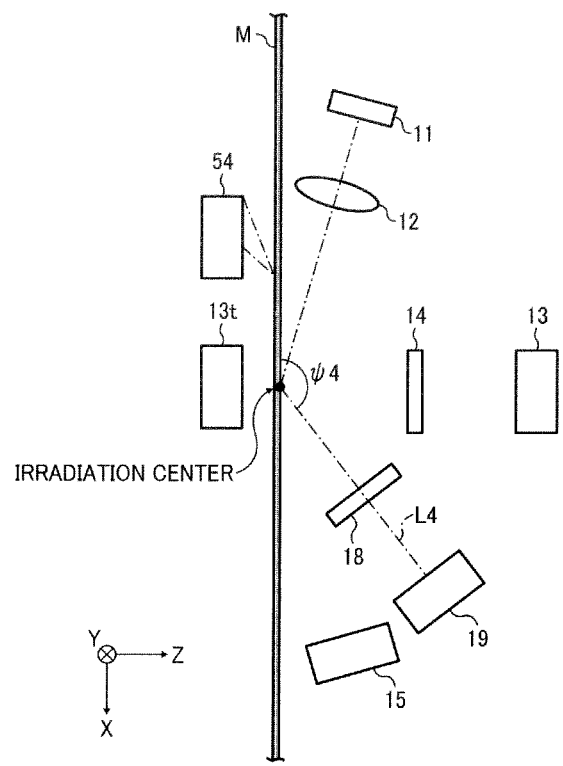
FIG. 52 illustrates a second modification of an optical sensor, according to the third example embodiment of the present invention.

FIG. 52 illustrates the second modification of an optical sensor, according to the third example embodiment. As illustrated in FIG. 52, for example, the optical sensor 2245 may further include the photosensor 19 and the polarizing filter 18. As illustrated in FIG. 52, the polarizing filter 18 is arranged on the optical path of reflection light including the surface diffuse reflection light and internal reflection light. The polarizing filter 18 transmits the p-polarized light and blocks the s-polarized light.

The photosensor 19 is arranged on the optical path of the light flux that has passed through the polarizing filter 18. The photosensor 19 receives the p-polarized light included in the internal reflection light.

As illustrated in FIG. 52, for example, the angle ψ4 between the surface of the recording paper M and a line LA, which is drawn from the irradiation center to the centers of the polarizing filter 18 and photosensor 19, is 150 degrees. Note that the center of the light source 11, the irradiation center, the centers of the polarizing filters, and the centers of the photosensors are disposed on substantially the same plane.

The brand determination processes performed by the processing device 110 in the case of the third modification according to the third example embodiment are described as follows. Assuming that the recording paper M is irradiated with the light flux emitted from the light source 11, the signal level of the signal output from the photosensor 19 is referred to as "S5".

(1) The signal output from the displacement sensor 54 is referred to, and when it is confirmed that the recording paper M is at a specified position, a plurality of light-emitting units of the light source 11 are switched on at the same time.

(2) The values of S1, S2, S5, and ST are calculated from the signals output from the photosensors.

(3) The number of the pulses St output from the displacement sensor 54 is measured when the recording paper M is pulled out.

(4) The light-emitting units of the light source 11 are switched off.

(5) The value of S5/S1 is calculated.

(6) The recording paper identification table is referred to, and the brand of the recording paper is determined based on the obtained values of S5/S1, S2, and at least one of ST and St.

(7) The printer controller 2090 is notified of the result of the determination. Then, the brand determination process is terminated.

In the second modification of the third example embodiment illustrated in FIG. 52, the values of S5/S1, S2, St, and ST are measured for every brand of recording paper compatible with the color printer 2000 and the results are stored in the ROM 112 of the processing device 110 as a recording paper identification table, in advance of shipment, for example, when adjustment processes are performed in the factory.

Figure 53:
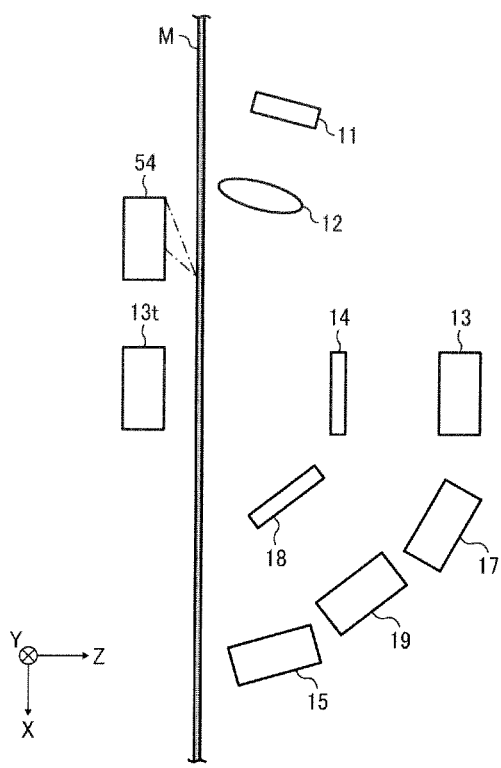
FIG. 53 illustrates a third modification of an optical sensor, according to the third example embodiment of the present invention.

FIG. 53 illustrates a third modification of an optical sensor, according to the third example embodiment. As illustrated in FIG. 53, for example, the optical sensor 2245 may further include the photosensor 17, the photosensor 19, and the polarizing filter 18.

The brand determination processes performed by the processing device 110 in the case of the third modification according to the third example embodiment are described as follows.

(1) The signal output from the displacement sensor 54 is referred to, and when it is confirmed that the recording paper M is at a specified position, a plurality of light-emitting units of the light source 11 are switched on at the same time.

(2) The values of S1, S2, S4, S5, and ST are calculated from the signals output from the photosensors.

(3) The number of the pulses St output from the displacement sensor 54 is measured when the recording paper M is pulled out.

(4) The light-emitting units of the light source 11 are switched off.

(5) The values of S5/S1 and S4/S2 are calculated.

(6) The recording paper identification table is referred to, and the brand of the recording paper is determined based on the obtained values of S5/S1 and S4/S2, and at least one of ST and St.

(7) The printer controller 2090 is notified of the result of the determination. Then, the brand determination process is terminated.

In the third modification of the third example embodiment illustrated in FIG. 53, the values of S5/S1, S4/S2, St, and ST are measured for every brand of recording paper compatible with the color printer 2000 and the results are stored in the ROM 112 of the processing device 110 as a recording paper identification table, in advance of shipment, for example, when adjustment processes are performed in the factory.

As described above, a plurality of photosensors are provided to detect the light diffused to several different directions, and the type of recording paper is determined based on the calculated values such as the ratio of the output values of the photosensors. Accordingly, precise determination becomes possible in spite of the existing disturbance light or stray light.

In the third modification of the third example embodiment, the printer controller 2090 may select several candidate brands of recording paper from the measurement values of S1 and S2, and these candidate brands can be narrowed down to a single brand in consideration of the values of 55/S1, S4/S2, and at least one of St and ST.

In the third modification of the third example embodiment, S5/S1 is used for determination when the values of S1 and S5 are obtained. However, no limitation is indicated therein. In a similar manner, no limitation is indicated to the use of S4/S2 when the values of S2 and S4 are obtained.

In the third example embodiment described above, the processing device 110 may notify the printer controller 2090 of the obtained values of S1, S2, St, and ST, and the printer controller 2090 may determine the brand of recording paper. In this case, a recording paper identification table is stored in the ROM of the printer controller 2090.

Figure 54:
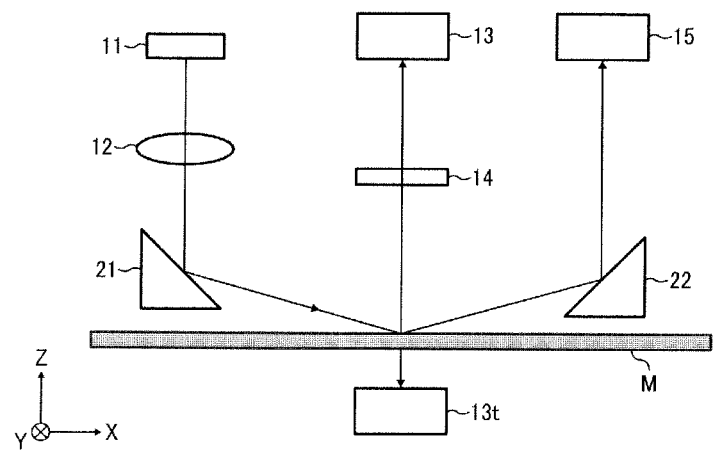
FIG. 54 illustrates Modification 4 of an optical sensor, according to the third example embodiment of the present invention.

FIG. 54 illustrates Modification 4 of an optical sensor, according to the third example embodiment. As illustrated in FIG. 54, for example, the optical sensor 2245 may further include two mirrors 21 and 22.

In Modification 4 of the third example embodiment, the light source 11 emits light flux in the direction parallel to the z-axis, and the collimate lens 12 is arranged so as to make the optical axis be parallel to the z-axis.

The mirror 21 deflects the light that has passed the collimate lens 12, and bends the optical path such that the angle of incidence on the recording paper M becomes 80 degrees.

The mirror 22 is equivalent to the mirror 21, and is arranged on the opposite side of the mirror 21 in the X-axis direction, with reference to the opening. Accordingly, the optical path of the surface regular reflection light from the recording paper M is bent such that the direction of travel becomes parallel to the z-axis.

The photosensor 15 is arranged on the +Z side of the mirror 22 to receive the surface regular reflection light whose optical path is bent by the mirror 22.

In Modification 4 of the third example embodiment described above, a member that supports the light source 11, the collimate lens 12, and the photosensor 15 in an inclined state is not necessary, and the electric circuit can be simplified. Accordingly, the cost and size may be reduced.

Figure 55:
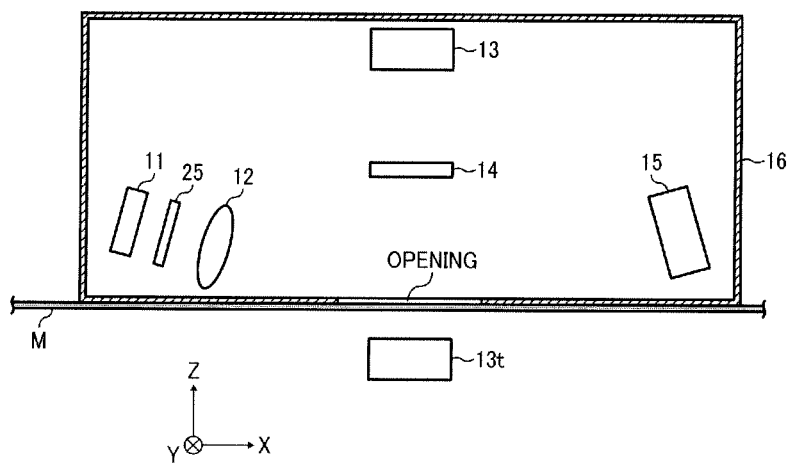
FIG. 55 illustrates Modification 5 of an optical sensor, according to the third example embodiment of the present invention.

FIG. 55 illustrates Modification 5 of an optical sensor, according to the third example embodiment. In the optical sensor described above, a conventional LD may be used in place of the surface emitting laser array. However, when a conventional LD is used, as illustrated in FIG. 55 as an example, the polarizing filter 25 needs to be arranged to obtain the s-polarized light from irradiation light.

For an optical sensor that identifies recording paper based on the reflection light quantity, the measurement reproducibility is crucial. In an optical sensor that identifies recording paper based on the reflection light quantity, a measurement system is arranged based on the premise that the surface at which measurement is performed and the surface of the recording paper are on the same plane. However, the surface of the recording paper may be inclined or floated up from the surface at which measurement is performed, and there are some cases in which the surface of the recording paper and the surface at which measurement is performed are not laid on the same plane. In such cases, the reflection light quantity varies, and stable and precise determination is difficult to make. Here, cases with regular reflection are described.

Figure 56C:
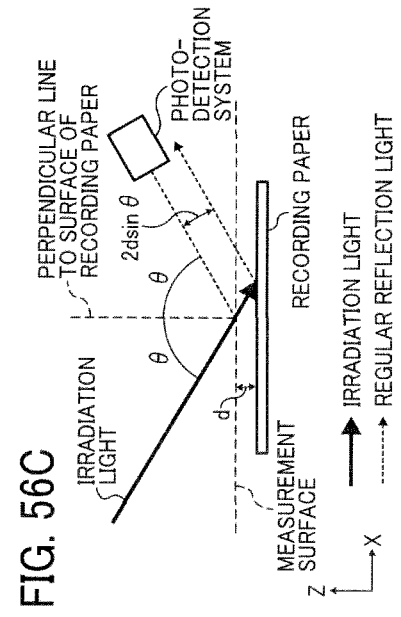
FIGS. 56A to 56C illustrate the changes in the amount of detection light caused due to the misalignment between the surface of recording paper and the surface at which measurement is performed, according to the third example embodiment of the present invention.
Figure 56A:
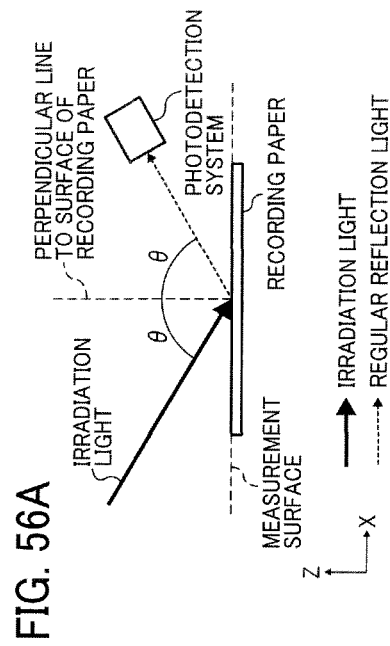
Figure 56B:
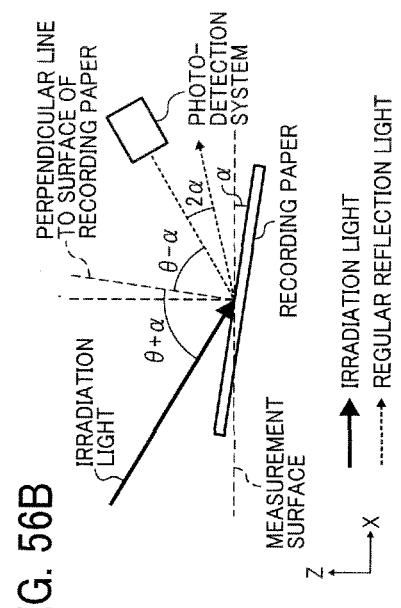

FIGS. 56A to 56C illustrate the changes in the amount of detection light caused due to the misalignment between the surface of recording paper and the surface at which measurement is performed, according to the third example embodiment FIG. 56A illustrates a case in which the surface at which measurement is performed and the surface of the recording paper are on the same plane. In this case, the photo-detection system can receive the regular reflection light.

FIG. 56B illustrates a case in which the surface at which measurement is performed is inclined by angle α with reference to the surface of the recording paper. If the relative positions of the irradiation system and the photo-detection system are the same as that of FIG. 56A, the photo-detection system receives light in the direction displaced from the direction of regular reflection by 2α. The intensity distribution of the reflection light shifts due to the displacement. Accordingly, assuming that the distance between the irradiation center and the photo-detection system is L, the photo-detection system receives light at a position that is displaced from the position at which the regular reflection light is received by L*tan 2α Moreover, the actual angle of incidence is displaced from a specified angle of incidence θ by α, and the reflectivity from the recording paper changes. Accordingly, the amount of detection light changes, and this makes detailed discrimination difficult.

FIG. 56C illustrates a case in which the surface at which measurement is performed is displaced in the height direction, i.e., in the Z-axis direction, by d with reference to the surface of the recording paper. The intensity distribution of the reflection light shifts due to the displacement when the relative positions of the irradiation system and the photo-detection system are the same as that of FIG. 56A. Accordingly, the photo-detection system receives light at a position that is displaced from the position at which the regular reflection light is received by 2d*sin θ. Accordingly, the amount of detection light changes, and this makes detailed discrimination difficult.

In the cases of FIGS. 56B and 56C, a condensing lens may be arranged in front of the photo-detection system such that the photo-detection system reliably detects the regular reflection light. Accordingly, even when the intensity distribution of the reflection light shifts, the reflection light can be condensed.

Alternatively, a photodiode (PD) whose light receiving area is sufficiently large may be used as a photosensor, or the beam diameter of the irradiation light may be narrowed, in order to deal with the problems caused when the surface of the recording paper and the surface at which measurement is performed are not laid on the same plane.

Alternatively, an array of PDs may be used as a photosensor such that the light receiving area becomes large enough to deal with the shift of the intensity distribution of the reflection light. In this case, even when the intensity distribution of the reflection light shifts, the largest signal among the signals received by the PDs may be handled as the signal of the regular reflection light. The light receiving area of each of the PDs may be made small so as to reduce the variation caused by the difference between the regular reflection light and the center of the light receiving area. By so doing, more accurate detection is achieved.

For the purpose of simplification, cases of regular reflection have been described. Although the changes in the amount of detection light occur due to the misalignment between the surface of recording paper and the surface at which measurement is performed, cases of surface diffuse reflection or internal diffuse reflection can be dealt with in a similar manner.

In the embodiments described above, cases in which the light source 11 includes a plurality of light-emitting units were described. However, no limitation in indicated therein, and the light source 11 may include only one light-emitting unit.

In the embodiments described above, it is desired that a condensing lens be provided in front of each of the photosensors. By so doing, the changes in the amount of detection light can be reduced.

In the embodiments described above, cases in which there is one paper feed tray were described. However, no limitation in indicated therein, and there may be a plurality of paper feed trays.

In the embodiments described above, an object to be identified is not limited to recording paper.

In the embodiments described above, cases in which an image forming apparatus includes four photoreceptor drums were described. However, no limitation in indicated therein.

In the embodiments described above, cases in which the color printer 2000 is used as an image forming apparatus were described. However, no limitation in indicated therein, and for example, an optical plotter or a digital photocopier may be used as an image forming apparatus.

Numerous additional modifications and variations are possible in light of the above teachings. It is therefore to be understood that within the scope of the appended claims, the disclosure of the present invention may be practiced otherwise than as specifically described herein. For example, elements and/or features of different illustrative embodiments may be combined with each other and/or substituted for each other within the scope of this disclosure and appended claims.

What is claimed is:

1. A sensor apparatus comprising:
   an irradiation system provided with a light source and configured to emit linearly polarized light of a first polarization direction onto a sheet-like object, in a direction oblique to a direction orthogonal to a surface of the object;
   a first photodetector arranged on an optical path of light that is emitted from the irradiation system and then is reflected at the object by regular reflection;
   a first optical element, arranged on an optical path of light reflected by diffuse reflection from an incidence plane of the object, configured to transmit linearly polarized light of a second polarization direction that is orthogonal to the first polarization direction;
   a second photodetector configured to receive the linearly polarized light transmitted through the first optical element; and
   a detection unit configured to determine at least one of basis weight and thickness of the object, on a basis of the linearly polarized light of the second polarization direction that is orthogonal to the first polarization direction of the light emitted by the irradiation system.

2. The sensor apparatus according to claim 1, wherein the detection unit includes a third photodetector configured to receive light that is emitted from the irradiation system and passes through the object.

3. The sensor apparatus according to claim 2, wherein the third photodetector is arranged on a back side of the object and disposed on an optical path of light that passes through the object, in a direction of a normal line drawn from a rear surface of the object.

4. The sensor apparatus according to claim 1, wherein the detection unit includes a mechanical thickness sensor configured to detect thickness of the object.

5. The sensor apparatus according to claim 4, wherein the irradiation system, the first, second, and third photodetectors, and the first optical element form an optical unit, and the optical unit is disposed opposite the thickness sensor with the object therebetween.

6. The sensor apparatus according to claim 4, wherein the irradiation system, the plurality of photodetectors, and the first optical element form an optical unit, and the optical unit and the thickness sensor are adjacent to each other in a direction parallel to a surface of the object.

7. The sensor apparatus according to claim 4, wherein the thickness sensor includes a first member having a reference plane member, a second member that presses the object against the reference plane member, and a detector that detects thickness of the object via the second member.

8. The sensor apparatus according to claim 1, further comprising a fourth photodetector arranged on an optical path of light reflected by diffuse reflection from an incidence plane of the object.

9. The sensor apparatus according to claim 8, further comprising:
   a second optical element, arranged on an optical path of light that is reflected by diffuse reflection from an incidence plane of the object, configured to transmit linearly polarized light of the second polarization direction; and
   a fifth photodetector configured to detect light that has passed through the second optical element.

10. The sensor apparatus according to claim 1, further comprising:

a fourth photodetector arranged on an optical path of light that is reflected by diffuse reflection from an incidence plane of the object;

a second optical element, arranged on an optical path of light that is reflected by diffuse reflection from an incidence plane of the object, configured to transmit linearly polarized light of the second polarization direction; and a fifth photodetector configured to detect light that has passed through the second optical element.

11. The sensor apparatus according to claim 10, wherein the first optical element and the second optical element are arranged, respectively, on an optical path of light reflected by diffuse reflection from the object, in a direction of a normal line drawn from a front surface of the object.

12. The sensor apparatus according to claim 1, wherein the light source includes a surface emitting laser array having a plurality of light-emitting units.

13. The sensor apparatus according to claim 1, further comprising a processor configured to identify the object based on output from the plurality of photodetectors and output from the detection unit.

14. The sensor apparatus according to claim 13, wherein the processor identifies the object based on output from the plurality of photodetectors, and when a plurality of candidates exist, the processor selects one candidate from the plurality of candidates based on output from the detection unit.

15. The sensor apparatus according to claim 13, wherein the processor identifies the object based on output from the detection unit, and when a plurality of candidates exist, the processor selects one candidate from the plurality of candidates based on output from the plurality of photodetectors.

16. The sensor apparatus according to claim 1, wherein the detection unit includes a third photodetector configured to receive light that is emitted from the irradiation system and passes through the object, and a mechanical thickness sensor configured to detect thickness of the object.

17. The sensor apparatus according to claim 16, further comprising a processor configured to identify the object based on output from the plurality of photodetectors and output from the detection unit, wherein the processor estimates thickness of the object based on output from the thickness sensor, and estimates basis weight of the object based on output from the third photodetector when estimated thickness is equal to or less than a prescribed value.

18. An image forming apparatus comprising:

an image forming unit configured to form an image on a recording medium;

the sensor apparatus according to claim 1 where the recording medium is an object; and an adjustment unit configured to adjust a condition for image formation, based on output from the sensor apparatus.

* * * * *